United States Patent [19]
Ishiguro et al.

[11] Patent Number: 5,434,061
[45] Date of Patent: Jul. 18, 1995

[54] PRODUCTION OF SACCHARIDE CARBOXYLIC ACIDS

[75] Inventors: Toshihiro Ishiguro, Toyono; Masahide Oka, Kawanishi; Takamasa Yamaguchi, Kobe; Ikuo Nogami, Nagaokakyo, all of Japan

[73] Assignee: Takeda Chemical Industries, Ltd., Osaka, Japan

[21] Appl. No.: 152,122

[22] Filed: Nov. 15, 1993

[30] Foreign Application Priority Data

Nov. 27, 1992 [JP] Japan .................. 4-318807
Mar. 11, 1993 [JP] Japan .................. 5-050652
Jul. 13, 1993 [JP] Japan .................. 5-173121

[51] Int. Cl.$^6$ ............... C12P 19/22; C12P 19/14; C12P 19/12; C12P 19/04
[52] U.S. Cl. .................... 435/100; 435/96; 435/98; 435/99; 435/101; 435/137; 435/138; 435/822
[58] Field of Search ......... 435/100, 137, 138, 101, 435/822, , 99, 98, 96

[56] References Cited

U.S. PATENT DOCUMENTS

4,876,195 10/1989 Shirafugi et al. .......... 435/137
4,877,735 10/1989 Nogami et al. .......... 435/138

FOREIGN PATENT DOCUMENTS

0150085  7/1986  European Pat. Off. .
0221707  5/1987  European Pat. Off. .
0248400 12/1987  European Pat. Off. .
62-228287 10/1987  Japan .
5-68542  3/1993  Japan .

*Primary Examiner*—Herbert J. Lilling
*Attorney, Agent, or Firm*—Wenderoth, Lind & Ponack

[57] ABSTRACT

A process for producing a saccharide carboxylic acid or a salt thereof characterized in that a microorganism belonging to the genus Pseudogluconobacter and capable of oxidizing a hydroxymethyl group and/or hemiacetal hydroxyl-associated carbon atom to a carboxyl group, or an artifact derived from the microorganism, is permitted to act on a hydroxymethyl and/or hemiacetal hydroxyl-containing saccharide or saccharide derivative to produce and accumulate the corresponding carboxylic acid and the carboxylic acid so accumulated is harvested and novel saccharide carboxylic acids produced by the above production method, and by the process, from a broad range of saccharides, saccharic acids having carboxyl groups derived from hydroxymethyl and/or hemiacetal OH groups can be produced with high selectivity and in good yield, the resultant saccharide acids are resistant to enzymatic degradation and have improved water solubility, among other characteristics.

9 Claims, 12 Drawing Sheets

PRODUCTION OF SACCHARIDE CARBOXYLIC ACIDS

FIELD OF THE INVENTION

The present invention relates to novel sugar (or saccharide) carboxylic acids and salts thereof (sometimes hereinafter referred to briefly as sugar carboxylic acids or saccharide carboxylic acids, including the salts) and to a process for producing novel sugar carboxylic acid compounds. More particularly, the invention relates to a process for producing carboxylic acids from the corresponding primary hydroxyl(hydroxymethyl group)-containing saccharides with high efficiency by means of a strain of microorganism of the genus Pseudogluconobacter, or a cell preparation derived therefrom, novel sugar carboxylic acids such that hydroxymethyl groups of the corresponding saccharides have been oxidized to carboxyl groups, a process for producing a sugar carboxylic acid which comprises oxidizing the hemiacetal hydroxyl-associated carbon atom of the corresponding hemiacetal hydroxyl-containing saccharide to a carboxyl group by means of said strain of microorganism of the genus Pseudogluconobacter, or a cell preparation derived therefrom, and novel sugar carboxylic acids such that at least one hemiacetal hydroxyl-associated carbon of the corresponding saccharides has been oxidized to a carboxyl group.

BACKGROUND OF THE INVENTION

As microbial enzymes which catalyze the oxidation of a hydroxymethyl group to a carboxyl group, there are known alcohol dehydrogenase derived from bacteria of the genus Acetobacter [Agric. Biol. Chem. 42, 2331 (1978)], bacteria of the genus Gluconobacter [Agric. Biol. Chem. 42, 2045 (1978)] or bacteria of the genus Pseudomonas [Biochem. J., 223, 921 (1984), methanol dehydrogenase derived from methanol bacteria (Agric. Biol. Chem. 54, 3123 (1990)] and so on. However, all of them are highly substrate-specific and there is no report ever indicating that they act on substrates other than alcohols such as methanol and ethanol.

Meanwhile, as microbial enzymes which act on sugars, such as D-sorbitol, L-sorbose, etc. (these sugars are hereinafter referred to collectively as sorbose), to catalyze the oxidation of hydroxymethyl to carboxyl, there are known D-sorbitol dehydrogenase [Agric. Biol. Chem. 46, 135 (1982)], sorbose dehydrogenase [Agric. Biol. Chem. 55, 363 (1991) and glucose dehydrogenase [Agri. Biol. Chem. 44, 1505 (1980) derived from bacteria of the genus Gluconobacter. However, all of them are highly substrate-specific and lack versatility. It has also been found that certain bacteria isolated from the soil and named *Pseudogluconobacter saccharoketogenes* produce 2-keto-L-gulonic acid (hereinafter referred to sometimes as 2KGA) (cf. Japanese Patent Application Kokai S-62-228288 and Kokai S-64-85088) and 2-keto-D-glucaric acid from D-glucose or the like (cf. Japanese Patent Application Kokai S-62-228287) in substantial quantities.

Referring to polysaccharides, dextran, for instance, is a generic name denoting many high molecular glucans predominantly composed of alpha-1→6 bonds as derivatized from sucrose by *Leuconostoc mesenteroides* and other organisms and a variety of chemical modifications have been attempted. However, by the routine chemical reactions, the object product can hardly be obtained with sufficiently high position selectivity, the formation of many byproducts being inevitable. Since many polysaccharides inclusive of dextran are respectively composed of several high molecular homologs varying in molecular weight, chemical modification is accompanied by side reactions to yield a complicated series of byproducts and it is often true that all of such products cannot be structurally identified (Biotransformations in Preparative Organic Chemistry; H. G. Davis et al, Academic Press).

Particularly, chemical oxidation of dextran with an oxidizing agent such as sodium hypochlorite, sodium hypobromite, chlorine, bromine or iodine has been attempted but the products have not been structurally elucidated for certain or the proposed structures have not been fully validated. Regarding the chemical oxidation of dextran, pertinent disclosure can be found in Patel et al, (Japanese Patent Application, Kokai S-61-233001, European Patent Application, Publication No. 0150085).

As mentioned above, the oxidation of hydroxymethyl-containing saccharides and other compounds with the aid-of microorganisms has heretofore been seriously restricted to monosaccharides and the like by the substrate-specificity of the microorganisms. Furthermore, as mentioned above, chemical modification of the hemiacetal hydroxyl and hydroxymethyl moieties of saccharides, particularly of oligosaccharides and polysaccharides, are accompanied by many side reactions and unavoidably require a complicated procedure for purification. Therefore, a more selective and efficient oxidation technology has been awaited in earnest. The object of the invention is, therefore, to provide a process for producing saccharic acids, viz. sugar carboxylic acids, comprising oxidizing at least one hydroxymethyl group and/or hemiacetal hydroxyl-associated carbon atom in high yield and with high selectivity by means of a microorganism showing a position specificity to a broad range of substrates for the ultimate goal of producing a number of industrially and socially useful substances.

SUMMARY OF THE INVENTION

Figure 1:
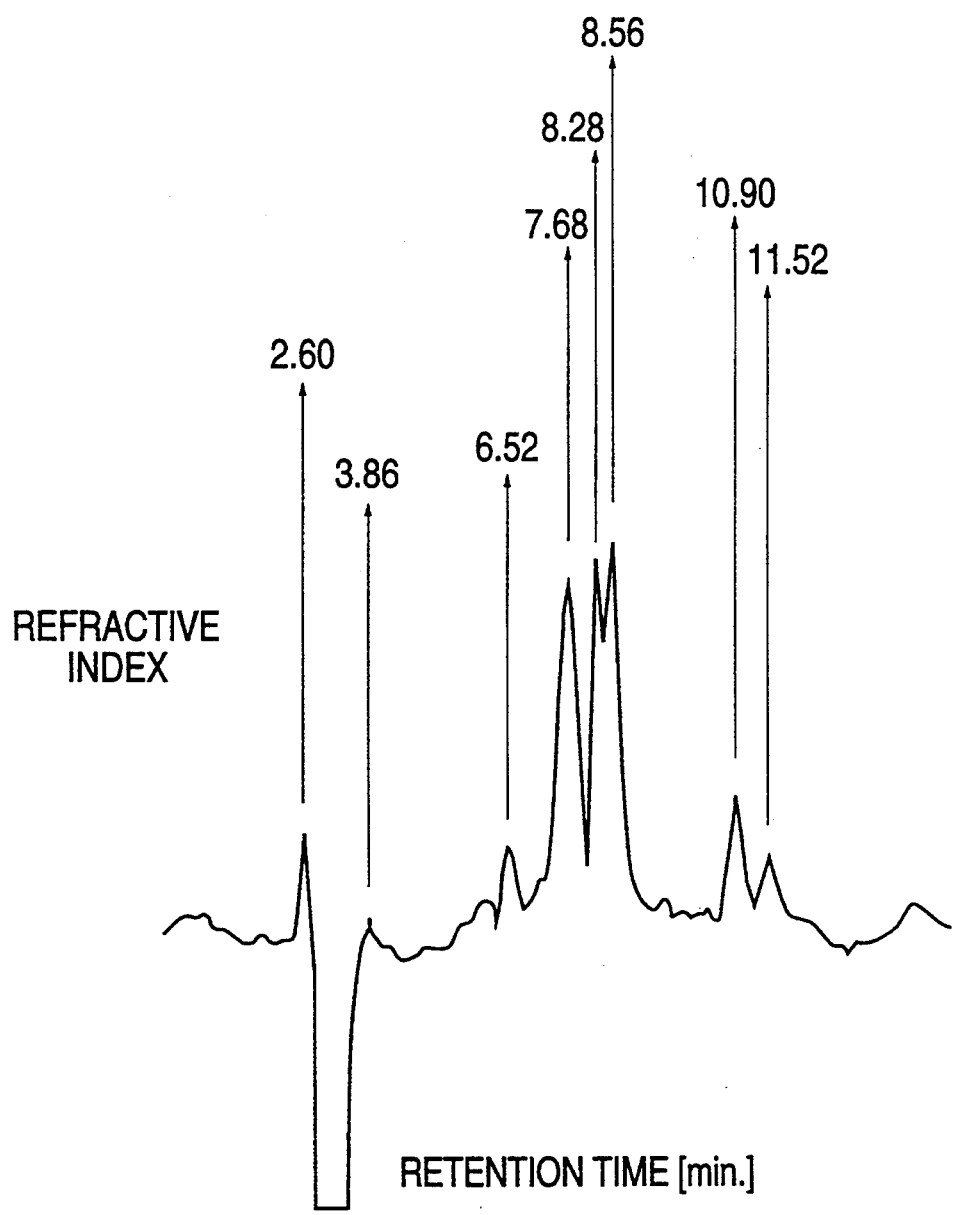
FIG. 1 shows the HPLC pattern (RI detection) of the glucuronic acid type steviol glycosides in mixture obtained in Example 5.

After an intensive exploration into the microbial world for accomplishing the above object, the inventors of the present invention discovered that *Pseudogluconobacter saccharoketogenes* oxidizes a broad spectrum of hydroxymethyl(—CH$_2$OH) and/or hemiacetal hydroxyl-containing saccharides and saccharide derivatives readily, in good yield and with high selectivity and that, to a great surprise, these microorganisms were very liberal in substrate specificity, thus being remarkably versatile bacteria. The present invention has been developed on the basis of the above findings.

The present invention is directed to:

1) A process for producing a saccharide carboxylic acid or a salt thereof which comprises permitting microorganism belonging to the genus Pseudogluconobacter and capable of oxidizing a hydroxymethyl group and/or a hemiacetal hydroxyl-attached carbon atom to carboxyl group or a cell preparation obtained therefrom to act on a hydroxymethyl- and/or hemiacetal hydroxyl-containing monosaccharide derivative, oligosaccharide, oligosaccharide derivative, polysaccharide or polysaccharide derivative to produce and accumulate the corresponding carboxylic acid and isolating said carboxylic acid and 2) novel saccharide carboxylic acids such that at least one hydroxymethyl group and/or hemiacetal hydroxy group of the corresponding saccharides or saccharide derivatives has been oxidized to carboxyl group.

DETAILED DESCRIPTION OF THE INVENTION

The microorganisms of the genus Pseudogluconobacter which can be employed in the present invention can be any strain of microorganism of said genus that is capable of oxidizing the hydroxymethyl group and/or hemiacetal hydroxyl carbon atom of saccharides and include the mutant strains obtainable by subjecting said microorganism to the conventional mutagenic treatment such as treatment with a chemical mutagen, e.g. nitrosoguanidine, ultraviolet radiation, genetic engineering and so on. Particularly preferred are strains of *Pseudogluconobacter saccharoketogenes*. Particularly, the following strains described in European Patent Application (EPA) 221,707 can be mentioned as typical examples.

○ *Pseudogluconobacter saccharoketogenes* K 591s: FERM BP-1130, IFO 14464
○ *Pseudogluconobacter saccharoketogenes* 12-5: FERM BP-1129, IFO 14465
○ *Pseudogluconobacter saccharoketogenes* TH 14-86: FERM BP-1128, IFO 14466
○ *Pseudogluconobacter saccharoketogenes* 12-13: FERM BP-1132, IFO 14482
○ *Pseudogluconobacter saccharoketogenes* 12-4: FERM BP-1131, IFO 14483
○ *Pseudogluconobacter saccharoketogenes* 22-3: FERM BP-1133, IFO 11484.

In the process of the invention, not only cells of any such strain of the genus Pseudogluconobacter but also any cell preparation that can be obtained by processing them can be equally employed. The cell preparation mentioned above may for example be a culture broth of the strain. The enzyme system produced by the microorganisms can also be employed. However, in the case of microorganisms of the genus Pseudogluconobacter, the enzyme is usually secreted intracellularly. It is, therefore, advantageous to allow the microbial cells as such to act on the substrate saccharide to produce the corresponding carboxylic acid. It is particularly preferable to employ resting cells. Such cells or a culture broth of the microorganism can be produced by the method described in Japanese Patent Application Kokai S-64-85088, for instance.

Thus, a slant culture is subjected to seed culture and main culture to prepare a fermentation broth. If necessary, this fermentation broth is centrifuged and the sediment is collected and washed a few times with saline. The washed sediment can then be used in the oxidation reaction. The microorganisms can be cultivated aerobically in a liquid medium containing nutrients which they can utilize, namely sources of carbon (carbohydrates such as glucose, sucrose, starch, etc. or organic materials such as peptone, yeast extract, etc.), sources of nitrogen (inorganic and organic nitrogenous materials such as ammonium salts, urea, corn steep liquor, peptone, etc.), inorganic salts (phosphates, thiosulfates and other salts of potassium, sodium, calcium, magnesium, iron, manganese, cobalt, copper, etc.) and, as trace nutrients, vitamins and coenzymes such as CoA, pantothenic acid, biotin, thiamin, riboflavine, FMN (flavine mononucleoside), etc., amino acids such as L-cysteine, L-glutamic acid, etc. and natural materials containing them. The culture broth thus obtained can be directly employed in the process of the invention. The cultivation can be carried out at pH 4–9 and preferably at pH 6–8.

The incubation time is dependent on the microbial strain used, medium composition and other conditions but is preferably 10 to 100 hours. The temperature range suited for cultivation is 10°–40° C. and preferably 25°–35° C. The objective compound can be produced with improved efficiency by adding a rare earth metal to the medium. The rare earth metal which can be thus added to the medium includes scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb) and lutetium (Lu). These rare earth metals can be respectively added in bulk, as flakes or in the form of a compound such as the chloride, carbonate, sulfate, nitrate, oxide or oxalate. These elements can be used independently or in combination, for example cerium carbonate and lanthanum chloride. Furthermore, crude products available in the course of isolation and purification of the elements can likewise be employed. The amount of rare earth elements to be added to the medium can be selected from the range not interfering with growth of the microorganism used and is generally 0.000001–0.1% (w/v) and preferably 0.0001–0.05% (w/v). Regarding the procedure for addition to the medium, these elements can be added intermittently or continuously during cultivation.

In practicing the invention, the substrate saccharide to be oxidized may be dissolved or suspended in water or a water-miscible solvent such as methanol, acetone, polyethylene glycol or the like and the resultant solution or suspension be contacted with the microorganism. The solvent can be used in an optional amount that will not retard the reaction. Thus, the preferred substrate concentration is generally 0.1–20% (w/v) and preferably 1–5% (w/v). The preferred temperature range for the microbial oxidation reaction of the invention is 10°–40° C. and preferably 25°–35° C. This reaction is preferably conducted under aerobic conditions, for example under airation sparging at a rate of 0.1–5 l/min., if necessary with stirring at 50–2000 rpm. The reaction time is dependent on the propensity of the primary hydroxyl group and/or hemiacetal hydroxy group of the substrate saccharide but ranges from 5 minutes to 3 days and, in many cases, from 1 to 24 hours. This reaction is preferably conducted under constant pH control. The recommended pH range is pH 4–9 and, for still better results, pH 6–8. For the pH control, any base that will not interfere, with the reaction can be employed. For example, not only inorganic salts such as sodium hydroxide, potassium hydroxide, calcium carbonate, magnesium hydroxide, ferrous hydroxide, etc. but also organic salts such as sodium morpholinoethanesulfonate, calcium morpholinoethanesulfonate, etc. can be employed. If desired, an anion exchange resin may be added to the reaction system so as to selectively control the reaction without resort to a neutralizer such as an alkali metal salt. This addition of an anion exchange resin is particularly suited in directing the reaction to selective formation of one-equivalent oxidation product. The anion exchange resin for this purpose may be any anion exchange resin that adsorbs the product carboxylic acid. Particularly preferred are anion exchange resins in the styrene or acrylic acid series. Thus, for example, Amberlite (trademark of Organo Co.)IRA-400, IRA-401, IRA-402, IRA-410, IRA-900, IRA-910, IRA-35, IRA-68, IRA-94S, etc. and Diaion (trademark of Mitsubishi Kasei) SA-10A, SA-20A, PA-306, PA-308, PA-406, WA-10, WA-11, WA-20, WA-30, etc. can be mentioned.

When the substrate saccharide (a hydroxymethyl- and/or hemiacetal OH-containing monosaccharide derivative, oligosaccharide, oligosaccharide derivative, polysaccharide or polysaccharide derivative) has disappeared in the reaction system, the stirring is discontinued and the anion exchange resin is separated from the reaction mixture. Then, the objective compound is eluted from the anion exchange resin with a suitable eluent. As examples of such eluent may be mentioned aqueous solutions of sodium chloride, alkali metal salts, etc. and aqueous solutions of acids such as hydrogen chloride, sulfuric acid, phosphoric acid, citric acid and so on. From the resultant eluate, the product sugar carboxylic acid can be separated and purified by the known isolation procedures or any procedures analogous thereto.

As examples of the saccharide whose primary hydroxyl (hydroxylmethyl) group or groups can be specifically oxidized to give the corresponding sugar carboxylic acid may be mentioned derivatives of monosaccharides such as D-glucose, D-fructose, D-galactose, D-ribose, D-mannose, L-sorbose, etc. [e.g. amino sugars such as D-glucosamine, N-acetyl-D-glucosamine, N-acetylchitobiose, tri-N-acetylchitotriose, etc., ascorbic acid-related compounds such as glycosyl-L-ascorbic acid, L-ascorbic acid, etc., nucleic acid-related compounds such as inosine, adenosine, uridine, guanosine, cytidine, thymidine, 2-deoxyinosine, 2-deoxyadenosine, 2-deoxyuridine, 2-deoxyguanosine, 2-deoxycytidine, 2-deoxythymidine, etc.], oligosaccharides such as streptozotocin (streptozocin), sucrose, lactose, palatinose, raffinose, lactosucrose, glucosylsucrose, galactosylsucrose, xylobiose, etc., starch saccharides such as maltotriose, maltotetrose, isomaltotriose, panose, maltitol, etc., amino sugars such as validamycin A, cellooligosaccharides such as cellobiose, cellotriose, cellohexose, etc., steviol glycosides such as stevioside, rebaudioside-A, rebaudioside-C, rebaudioside-D, rebaudioside-E, dulcoside-A, rubusoside [the compound of formula (II), below, wherein $R_1=\beta$-Glc, $R_2=-\beta$Glc], etc., oligosaccharide derivatives such as mogrosides, etc., and polysaccharides and their derivatives such as cyclodextrin, soluble starch, dextrin, dextran, $\beta$-1,3-glucans and so on.

Incidentally, the oligosaccharide and polysaccharide derivatives include saccharic acids such that the carbon atoms associated with hemiacetal hydroxyl groups of oligosaccharides and polysaccharides have been oxidized to carboxyl groups by the process of the invention which is described hereinafter.

The saccharide whose hemiacetal hydroxyl moiety is specifically oxidized by the process of the invention includes, among others, dextran, cellulose, chitin, amylose, amylopectin, maltotriose, panose, isomaltose, cellobiose, lactose, maltose and so on.

Among the sugar carboxylic acids which can be obtained from such saccharides, the following are novel compounds:

a saccharide carboxylic acid such that at least one hydroxymethyl group of palatinose has been oxidized to carboxyl group or a salt thereof;

a saccharide carboxylic acid such that at least one hydroxymethyl group of sucrose has been oxidized to carboxyl group or a salt thereof;

a saccharide carboxylic acid such that at least one hydroxymethyl group of D-trehalose has been oxidized to carboxyl group or a salt thereof;

a saccharide carboxylic acid such that at least one hydroxymethyl group of maltosyl-$\beta$-cyclodextrin has been oxidized to carboxyl group or a salt thereof;

a saccharide carboxylic acid such that at least one hydroxymethyl group of 2-O-$\alpha$-D-glucopyranosyl-L-ascorbic acid has been oxidized to carboxyl group or a salt thereof;

a saccharide carboxylic acid such that at least one hydroxymethyl group of streptozotocin has been oxidized to carboxyl group or a salt thereof;

a saccharide carboxylic acid such that at least one hydroxymethyl group of heptulose has been oxidized to carboxyl group or a salt thereof;

a saccharide carboxylic acid such that at least one hydroxymethyl group of maltodextrin of formula (I)

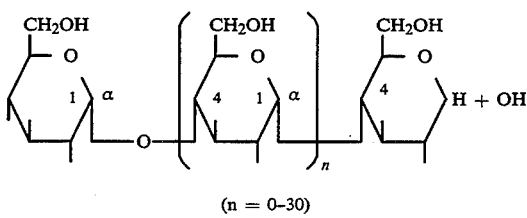

(n = 0–30)

has been oxidized to carboxyl group or a salt thereof; a saccharide carboxylic acid such that at least one hydroxymethyl group of a steviol glycoside of formula (II)

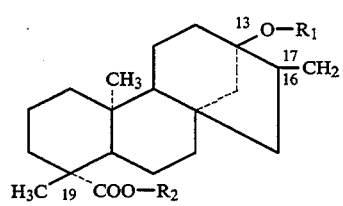

[wherein $R_1$ = -β-Glc-2-β-Glc, -β-Glc-2-β-Glc,
                                         \
                                         3-β-Glc
-β-Glc-2-α-Rha, -β-Glc-2-α-Rha or -β-Glc;
                 \
                 3-β-Glc
$R_2$ = -β-Glc or -β-Glc-2-β-Glc has been oxidized to carboxyl group or a salt thereof; a saccharide carboxylic acid such that at least one hydroxymethyl group of validamycin A of formula (III)

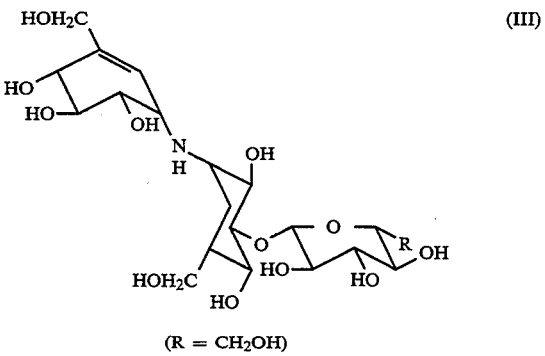

(R = CH₂OH)

has been oxidized to carboxyl group or a salt thereof; a saccharide carboxylic acid such that at least one hydroxymethyl group of mogroside has been oxidized to carboxyl group or a salt thereof; a saccharide carboxylic acid of formula (VIII)

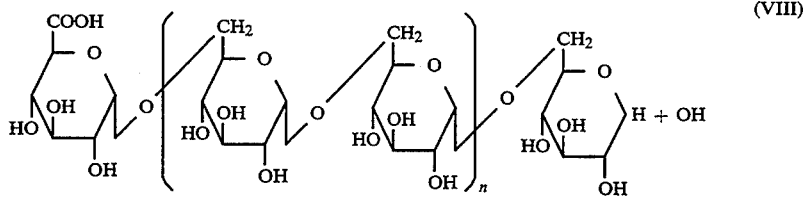

(wherein n=1–50, preferably 10–15) such that hydroxymethyl group of dextran has been oxidized to carboxyl group [e.g. dextranylglucuronic acid ( also known as glucuronyldextran or dextran-glucuronic acid)], a salt thereof or a coordination compound or complex thereof with a metal salt (hereinafter referred to briefly as a complex) thereof and a saccharide carboxylic acid of formula (IX)

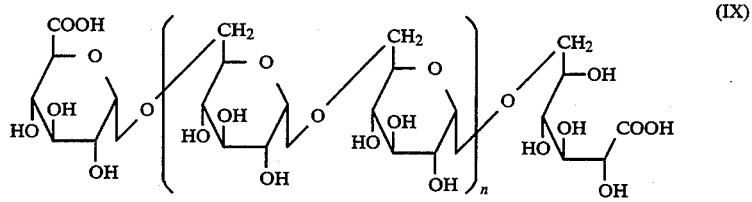

(wherein n=1–50, preferably 10–15) such that the hemiacetal hydroxyl-attached carbon atom of dextranylglucuronic acid (also called dextranglucuronic acid) has been oxidized to carboxyl group [e.g. glucuronyl dextranylgluconic acid] or a salt thereof or a metal salt complex thereof are industrially useful novel compounds.

In the oxidation of such a substrate saccharide using cells of said microorganism of the genus Pseudogluconobacter or a cell preparation obtained-derived therefrom, the saccharide is oxidized with position-selectivity and in a stepwise manner reflecting the number and propensities of its primary hydroxyl groups or hemiacetal hydroxyl groups to give the corresponding saccharide carboxylic acid with high specificity and this is also a characteristic of the oxidation reaction using cells or cell preparations of microorganisms of the genus Pseudogluconobacter.

Where the objective compound can be isolated easily microorganisms of the genus Pseudogluconobacter may be cultivated in a medium containing the substrate saccharide. The cultural conditions may be identical with those mentioned above for the preparation of a culture broth.

The saccharide carboxylic acid thus produced and accumulated can be separated and purified by the known procedures or procedures analogous thereto. For example, the objective compound can be separated and purified by such procedures as filtration, centrifugation, treatment with activated carbon or an absorbent, solvent extraction, chromatography, precipitation or salting-out, etc., either applied independently or in a suitable combination.

When the oxidation reaction is conducted in the presence of an anion exchange resin as described above, the resin is separated from the reaction mixture by decantation, centrifugation or the like and, then, elution is carried out with a suitable eluent. The resultant fractions rich in the objective compound are collected and subjected to the above-mentioned isolation procedure or procedures for isolation and purification.

The complex of dextran-carboxylic acid with an iron salt can be generally produced by the known method for the production of a dextran-iron salt complex or a method analogous thereto. For example, it can be produced by reacting dextran-carboxylic acid with a iron salt sol, e.g. ferric hydroxide sol. Thus, a colloidal solution or suspension can be produced preferably by adding dextran carboxylic acid to purified ferric hydroxide sol free from salts and making the mixture adjusted to pH 8.0–10 under elevated temperature conditions, for example by heating in an autoclave at 100° C.–120° C. for 30 minutes.

By this process, the dextran-carboxylic acid-iron salt complex is formed through such processes as Fe salt formation, chelation/hydration, etc. As will be described hereinafter, the elemental iron content of this colloidal suspension of iron salt complex in water is about 50–250 mg/ml on a solution basis and, if desired, an Fe-rich complex can be obtained from an Felean complex by evaporation, concentration or the like. The Fe-rich iron salt complex remains stable for quite a long time and is particularly characterized in that it retains its colloidal state in aqueous medium with good stability.

The resultant dextran-carboxylic acid-iron salt (e.g. ferric hydroxide) complex can be diluted with distilled water for injection, physiological saline or the like and administered parenterally to animals. As alternatives, it can be formulated with a pharmaceutically acceptable diluent or excipient and processed by the per se known pharmaceutical procedures to provide tablets, powders, granules, capsules, emulsions, solutions, premixes, syrups, etc. for administration by the oral route. Moreover, these dosage forms as such or dispersions thereof in vehicles can be put to use as incorporated in feed or drinking water. Furthermore, it is possible, if desired, to formulate each material with a pharmaceutically acceptable diluent or excipient, dilute the formulation extemporaneously to provide a unit dosage and administer it as admixed with feed or drinking water. Moreover, the independently formulated preparations can be independently administered concurrently or at staggered times to the same subject by the same route or different routes.

In accordance with the present invention, each carboxylic acid can be obtained as a free compound or in the form of a salt. Of course, when a free acid is obtained, it can be converted to a salt and when a salt is obtained, it can be converted to the free acid or a different salt, all by the per se known procedures. It is also possible to incorporate iron, an alkali metal, e.g. lithium, sodium, potassium, or an alkaline earth metal, e.g. magnesium, calcium, etc., in the culture medium so that the saccharide carboxylic acid may be converted to the corresponding salt as it is produced and accumulated. The resultant product can be identified by the routine techniques such as elemental analysis, melting point determination, polarimetry, infrared spectrometry, NMR spectrometry, chromatography and so on.

The saccharide carboxylic acids thus obtained in accordance with the invention proved to possess unique properties and are thus applicable in a variety of fields. By way of illustration, while steviol glucosides include the following compounds.

| Steviol glycoside | In the formula (II) $R_1$ | $R_2$ |
|---|---|---|
| Steviodide | $-\beta$-Glc-2-$\beta$-Glc | $-\beta$-Glc |
| Rebaudioside-A | $-\beta$-Glc-2-$\beta$-Glc \ 3-$\beta$-Glc | $-\beta$-Glc |
| Rebaudioside-C | $-\beta$-Glc-2-$\alpha$-Rha \ 3-$\beta$-Glc | $-\beta$-Glc |
| Rebaudioside-D | $-\beta$-Glc-2-$\beta$-Gl \ 3-$\beta$-Glcc | $-\beta$-Glc-2-$\beta$-Gl |
| Rebaudioside-E | $-\beta$-Glc-2-$\beta$-Gl | $-\beta$-Glc-2-$\beta$-Gl |
| Dulcoside-A | $-\beta$-Glc-2-$\alpha$-Rha | $-\beta$-Glc |
| Rubusoside | $-\beta$-Glc | $-\beta$-Glc | the corresponding steviol glycoside derivatives in the glucuronic acid form are invariably novel compounds and each has been found to have an improved, intense and sumptuous sweet taste. They are expected to enjoy use as high-sweetness food materials having a low-calorie feature and a dental anticaries effect as well as resistance to enzymes in confections, nonalcoholic beverages, pickles, ice confections, etc. in the same manner as the conventional sweeteners. Moreover, since these compounds feature improved solubility, low toxicity, and good disintegratability and degradability, they are capable of ameliorating the tastes of drugs and, therefore, can be used as corrigents. Thus, for example, they can be incorporated in tablets, powders and other preparations. Moreover, the saccharide carboxylic acids derived from $\beta$-maltosyl-$\beta$-cyclodextrin are the first saccharide Carboxylic acids in the cyclodextrin series and feature a remarkably improved water solubility (solubility > 200g/100 ml, $H_2O$, 25° C.). Therefore, when a sparingly soluble drug such as prostaglandins, steroids, barbituric acid, etc. is clathrated with a saccharide carboxylic acid derived from $\beta$-cyclodextrin, the product shows improved water solubility and can be used as an injection. For purposes of clathration, these saccharide carboxylic acids can be used in the same manner as the hithertoknown clathrate materials. $\beta$-D-Fructosyl-(2→1)-$\alpha$-D-glucuronic acid and $\alpha$-D-glucuronyl-(1→2)-$\beta$-D-6-fructulonic acid, both of which can be derived from sucrose, are novel sucrose derivatives devoid of sweetness and have been found to be resistant to degradation by glucosidase, pectinase, glucuronidase and invertase. Compared with sucrose, they are less susceptible to enzymes. Therefore, these compounds are of value as hard-to-digest, low-calorie sucrose derivatives to be added to confections, cakes, ice confections and so on. Their calcium, magnesium and iron salts are of use as the corresponding metal ion absorption improving agents. Therefore, these compounds can be added to biscuits, cakes, nonalcoholic beverages, etc. to provide foods and drinks for the prevention of osteoporosis.

Furthermore, $\beta$-D-fructosyl-(6→1)-$\alpha$-D-glucuronic acid and $\alpha$-D-glucuronyl-(6→1)-$\alpha$-D-fructulonic acid which are obtainable by oxidizing palatinose are of use as hardly digestible, low-calorie dental anticaries agents. Therefor, these compounds can used in various foods such as chewing gums and other confections in the same manner as the ordinary sweeteners and flavors. Moreover, $\alpha$-D-glucuronyl-(7→1)-$\alpha$-D-glucuronic acid derived from D-trehalose is of value as a hardly digestible humectant or a stabilizer for antibody preparations. Meanwhile, $\beta$-amino-2-deoxy-D-glucuronic acid which can be obtained by oxidizing D-glucosamine is of use as a highly moisture-retaining cosmetic base.

Meanwhile, among the acids obtainable by oxidizing inosine and other nucleosides, 5'-carboxyinosine and 5'-carboxyadenosine, in particular, are of value as condiments having improved flavorant characteristics and stability against enzymatic degradation. These derivatives can be utilized as ingredients of foodstuffs and condiments, particularly for seasoning storable foods.

Moreover, 1-carboxy-2,7-anhydro-$\beta$-D-altroheptulose obtainable by oxidizing 2,7-anhydro-$\beta$-D-altroheptulose has a mild sweet taste and can be used as a solubilizer for iron, calcium and magnesium in biscuits and other confections, nonalcoholic beverages and so on. The saccharide carboxylic acids derived from steptozotocin can be used as anticancer agents resistant to enzymes. Moreover, to exploit their antimicrobial activity, these derivatives can be used, either as they are or as appropriately diluted, in the disinfection and sterilization of hospital wards, hands and feet and so on. The mogroside-derived carboxylic acids are of value as high-sweeteners for addition to nonalcoholic beverages, confections and so on.

The saccharide carboxylic acid obtainable by oxidation of maltodextrin can be incorporated, as hardly digestible, low-energy food material, in confections, cakes, ice confections, etc. in the per se known manner.

Moreover, dextranylglucuronic acid which can be obtained by oxidizing the hydroxymethyl groups of dextran to carboxyl groups is not only of use as a pharmaceutical additive similar to dextran but even more stable and functional and exhibits its excellent characteristic as a stabilizer of ferric hydroxide sol. Furthermore, glucuronyldextranylgluconic acid which are obtainable by oxidizing the hydroxymethyl group of dextranylgluconic acid to carboxylic group or the carbon atom with the hemiacetal hydroxyl group attached thereto of dextranylglucuronic acid to carboxyl group, as well as salts thereof, are of use as a pharmaceutical base and can also be used as a viscosity retaining agent for food in the same manner as dextran. The metal salt which forms a complex with dextranylglucuronic acid or glucuronyldextranylgluconic acid, or a salt thereof, includes monovalent, divalent and trivalent metal salts, such as salts of calcium, magnesium, iron, sodium, lithium, potassium and so on. Particularly the complexes with iron compounds such as ferric hydroxide can be used for iron supplementation as antienemics in asiderotic anemia in the same manner as dextran-iron combination drugs.

Validamycin A is a compound of the formula (III) presented hereinbefore which has fungicidal activity against the causative organism of sheath blight in the rice plant. Since the oxidation product of validamycin A according to the invention is expected to be resistant to the glucosidase of the causative organism, it may be used as a long-acting derivative of validamycin A which may prove of use as an agricultural fungicide of prolonged action. The saccharide carboxylic acid derived from ascorbic acid is also more resistant to enzymatic degradation and therefore finds application as an enzyme-resisting antioxidant. For use as an antioxidant, it can be used as incorporated in iron-containing foods in the same manner as ascorbic acid.

Thus, the saccharide carboxylic acids made available by oxidizing the hydroxymethyl groups and/or hemiacetal hydroxyl-associated carbon atoms of various saccharides in accordance with the invention have some or other characteristics not found in the substrate saccharides and can find application in uses not heretofore envisaged.

Compared with the substrate hydroxymethyl-containing saccharides, the saccharide carboxylic acids of the invention derived by oxidizing at least one hydroxymethyl group to a carboxyl group are more enzymatically stable and more readily soluble in water and, if desired, can be converted to metal salts. Therefore, in the field of food, they are expected to be of use as diet food materials which are hard to digest and low in energy value or agents, for improving the absorption of metals. To a great surprise, the carboxylic acids derived from steviol glycosides (stevioside, rebaudiosides, rubusoside, etc.) are 100–250 times as sweet as sucrose and have savory tastes devoid of the bitterness and objectionable aftertaste of the substrate stevioside, rubusoside, etc. and are of value as substantially non-energy-providing sweeteners.

The carboxylic acids of the invention as derived by oxidizing the hydroxymethyl groups of cyclodextrins have very favorable characteristics such as high solubility, low toxicity, good disintegrability and degradability and can be used for clathrating liposoluble drugs, fatty acids, basic drugs and the like. Since such clathration achieves the solubilization, stabilization and improved taste of the active ingredient, the product can be used as a corrigent. Specifically, it can be used as an improved functional base for pharmaceutical preparations such as tablets, capsules, pills, powders, granules, ointments, injections, syrups, suspensions, nose-drops and so on.

Thus, the present invention enables the oxidation of hydroxymethyl to carboxyl in a broad spectrum of saccharides and, hence, the provision of many novel saccharide carboxylic acids.

Furthermore, the saccharide carboxylic acids obtainable by oxidizing at least one hemiacetal hydroxyl-associated carbon atom to a carboxyl group in accordance with the invention are more enzymatically stable and have improved water solubility as compared with the hemiacetal OH-containing substrates and, if desired, can be converted to metal salts so that they are expected to be of use, in the field of food, as hard-to-digest, low energy-providing diet foods or for improvement of metal absorption. In the pharmaceutical field, they can be used in enteric preparations by taking advantage of their stabilizing effect on active ingredients and low enzymatic degradability.

In accordance with present invention, saccharide carboxylic acids such that the hydroxymethyl groups and/or hemiacetal hydroxyl-associated carbon atoms of a broad spectrum of saccharides have been oxidized to free carboxyl groups can be produced with high selectivity and in good yield. The resulant carboxylic acids are highly stable against enzymes and have improved water-solubility, to mention only a few outstanding characteristics.

The following examples are intended to describe the present invention in further detail but should not be construed as defining the scope of the invention.

EXAMPLE 1

Production of sodium β-D-fructosyl-(2→1)-α-D-glucuronate

One loopful of *Pseudogluconobacter saccharoketogenes* TH14-86 was transferred from a slant culture to a 200 ml smooth-walled flask containing the medium (20 ml) described below and precultured on a rotary shaker at 30° C. for 1 day. Then, 1 ml of the culture per 20 ml medium was shake-cultured at 30° C. for 20 days to prepare a seed culture. On the other hand, 1 loopful of *Bacillus megaterium* IFO 12108 was transferred from a slant culture to a 200 ml smooth-walled flask containing the medium (20 ml) described below and shake-cultured at 30° C. for 2 days.

Jar fermentation was then carried out under the following conditions. Thus, 100 ml of the above seed culture (seed medium) of TH14-86 and 1.5 ml of the seed medium of *Bacillus megaterium* were added to the main culture medium described below and shake culture was carried out at 30° C. for about 20 hours to provide a cell suspension of *Pseudogluconobacter saccharoketogenes* TH-14-86.

Cellular reaction:

A Biot's 5-liter jar fermentor was charged with a solution of 30 g sucrose in 200 ml sterilized water followed by addition of 1 l of the above cell suspension and 800 ml of sterilized water to make a total of 2 liters. Under aeration at 1 l/min. and stirring at 800 rpm, cultivation was carried out at 32° C. with 10% NaOH being added dropwise with the progress of reaction on an automatic mode so as to control the pH of the system at 6.3. The substrate was converted to the monocarboxylic acid in 2 hours.

Separation and purification:

Two liters of the above reaction mixture was centrifuged at 8000 rpm to remove the cells and the supernatant was passed columnwise over activated carbon (special-grade Shirasagi chromatographic charcoal, 400 g). The column was washed with water (1.2 l) and, then, elution was carried out with 3 l of water. The objective compound fractions were pooled and concentrated under reduced pressure to provide 19.70 g of sodium β-D-fructosyl-(2→1)-α-D-glucuronate as white powder.

Na salt: in $D_2O$ (90MHz), δppm: 61.39, 62.84, 71.48, 72.42, 73.09, 73.65, 74.65, 76.88, 82.01, 92.70, 104.18, 176.49.

Production of magnesium β-D-fructosyl-(2→1)-α-D-glucuronate

In 10 ml of water was dissolved 1.89 g of sodium β-D-fructosyl-(2→1)-α-D-glucuronate and the solution was passed through a IR-120 ($H^+$-form) column (50 ml). To the effluent was added 0.103 g of magnesium oxide and the mixture was stirred for 10 minutes. The mixture was then filtered through a millipore filter (Type GS, 0.22 μm) and the filtrate was concentrated. The resultant syrup was treated with ethanol-acetone to provide 1.45 g of magnesium β-D-fructosyl-(2→1)-α-D-glucuronate as white powder.

Elemental analysis for $C_{24}H_{38}O_{24}Mg \cdot 6H_2O$
Calcd.: C, 34.20; H, 5.98
Found: C, 34.33; H, 5.82

| Medium compositions | |
|---|---|
| [for TH14-86] | |
| Seed medium (in common for 1st and 2nd cultures) | |
| Lactose | 1% |
| Yeast extract (Prodivel) | 1% |
| $(NH_4)_2SO_4$ | 0.3% |
| Corn steep liquor | 3% |
| $CaCO_3$ (Super) | 2% |
| pH before addition of $CaCO_3$ = 7.0 | |
| [For *Bacillus megaterium*] | |
| [Seed medium] | |
| Sucrose | 4% |
| Proflo [N source, Tradas Protein (T & P)] | 4% |
| $K_2HPO_4$ | 0.65 |
| $KH_2PO_4$ | 0.55 |
| NaCl | 0.05 |
| $(NH_4)_2SO_4$ | 0.05 |
| $MgSO_4 \cdot 7H_2O$ | 0.005 |
| Calcium pantothenate | 0.025 |
| pH before sterilization = 7.0 | |
| [Main medium] | |
| Sucrose | 0.05%, independently sterilized |
| Corn steep liquor | 2%, independently sterilized |
| $(NH_4)_2SO_4$ | 0.3%, independently sterilized |
| $FeSO_4 \cdot 7H_2O$ | 0.1%, independently sterilized |
| Vitamin $B_2$ | 1 mg/l |
| pH before sterilization = 7.0 | |
| Sorbose | 10%, independently sterilized |
| $LaCl_3$ | 0.01%, independently sterilized |
| $CaCO_3$ (Super) | 4% independently sterilized |

EXAMPLE 2

Production of α-D-glucuronyl-(1→2)-β-D-6-fructulonic acid.

The sodium, magnesium and calcium salts of α-D-glucuronyl -(1→2)-β-D-fructulonic acid were produced in the same manner as Example 1.

Sodium salt: white powder
$^{13}C$-NMR($D_2O$) ppm: 61.98, 71.96, 73.02, 73.35, 73.69, 76.37, 77.03, 79.82, 93.97, 105.80, 175,03, 175.70.

Magnesium salt: white powder
Elemental analysis for $C_{12}H_{16}O_{13}Mg \cdot 5H_2O$
Calcd.: C, 29.86; H, 5.43
Found: C, 29.76; H, 5.51

Calcium salt: white powder
Elemental analysis for $C_{12}H_{16}O_{13}Ca \cdot 3H_2O$
Calcd.: C, 31.17; H, 4.80
Found: C, 31.26; H, 4.99

EXAMPLE 3

To 1l of the cell suspension of *Pseudogluconobacter saccharoketogenes* described in Example 1 was added 30g of palatinose as well as 1l of sterilized water and the reaction was carried out at 32° C. and 800 rpm with aeration at the rate of 1.6 l/min. for 1 hour. This reaction mixture was centrifuged at 8000 rpm to remove the cells and the supernatant was subjected to activated carbon (special-grade Shirasagi chromatographic charcoal, 400 g) column chromatography. The column was washed with water (2 l) and elution was carried out with 10% methanol-$H_2O$ (4 l) and further with 50% methanol-$H_2O$ (4 l). The fractions were pooled, concentrated and lyophilized to provide 35.8 g of sodium β-D-fructosyl-(6→1)-α-D-glucuronate.

This sodium salt was passed through an IR 120 (H+-form) column and the effluent was concentrated to provide β-D-fructosyl-(6→1)-α-D-glucuronic acid.

$^{13}$C-NMR($D_2O$) ppm: 63.35, 68.60, 71.78, 72.52, 72.77, 73.45, 75.14, 75.99, 79.53, 98.81, 102.21, 176.93.

Elemental analysis for $C_{12}H_{20}O_{12} \cdot 4.5H_2O$
Calcd.: C, 32.96; H, 6.68
Found: C, 33.17; H, 5.84

EXAMPLE 4

Using the following substrate compounds (parenthetized), the corresponding carboxylic acids were produced by the same procedures as described in Example 3.

TABLE 1
List of Reaction Products

| Compound | $^{13}$C-NMR | Other characteristic data |
|---|---|---|
| α-D-Glucuronyl-(6→1)-α-D-fructulonic acid (palatinose) | Na salt: in $D_2O$ (90 MHz) δ ppm: 68.01, 71.76, 72.46, 72.69, 73.40, 74.90, 78.72, 79.69, 98.74, 100.31, 176.80, 176.84 | Elemental analysis Calcd. for $C_{12}H_{16}OBNa_2 \cdot 2H_2O$ C, 32.01: H, 4.48 Found: C, 32.04: H, 4.45 |
| 2-Oα-D-Glucuronyl-D-ascorbic acid (glucosylascorbic acid) | Ca salt: in $D_2O$ (90 MHz) δ ppm: 57.94, 62.88, 69.91, 71.51, 72.15, 172.78, 72.96, 78.82, 99.46, 115.34, 176.49, 176.88. | Elemental analysis Calcd. for $C_{12}H_{16}O_{13}Ca \cdot 4.5 H_2O$ C, 29.70; H, 4.36 Found: C, 29.59; H, 4.69 |
| 6-O-α-D-glucuronyl-(1→4)-[α-D-glucosyl-β-cyclodextrin [also referred to as sodium O-cyclomaltoheptaos yl-(6→1)-D-α-glucosyl-(4→1)-O-α-D-glucuronate] (6-0-α-maltosyl-β-cyclodextrin) | Na salt: in $D_2O$ (90 MHz) δ ppm: 60.59, 60.66, 60.74, 60.83, 60.92, 60.95, 61.03, 70.86, 70.93, 71.01, 71.04, 71.08, 71.18, 71.21, 71.29, 71.33, 71.39, 71.47, 71.53, 71.59, 72.21, 72.25, 72.28, 72.35, 72.41, 72.52, 72.63, 72.79, 72.95, 73.13, 73.22, 73.27, 73.37, 73.53, 73.71, 73.80, 78.71, 78.77, 81.58, 81.61, 81.68, 81.71, 81.86, 81.93, 81.99, 82.06, 82.09, 100.54, 100.58, 102.24, 102.34, 102.43, 102.49, 176.41, | Elemental analysis Calcd. for $C_{54}H_{87}O_{46}Na \cdot 09H_2O$ C, 38.71; H, 6.43 Found: C, 38.87; H, 6.47 m.p.: >260° C. (decompn.) $[\alpha]_D^{20} = +146.9°$ (c = 0.61% $H_2O$) Solubility: >200 g/100 ml (25° C., $H_2O$) [Control: 6-O-α-D glucosyl-(1→4)-αD-glucosyl-β-cyclodextrin 150 g/100 ml (25° C., $H_2O$) 0.1 N HCl solution, half time at 60° C.: 8 hr [Control: 6-O-α-D glucosyl-(1→4)-α-D-glucosyl-β-cyclodextrin 5 hr)] Hemolytic activity: Concentration causing 50% hemolysis of rabbit erythrocytes in phosphate buffer (pH 7.4) at 37° : 11 mM |

TABLE 2
List of Reaction Products

Figure 7:
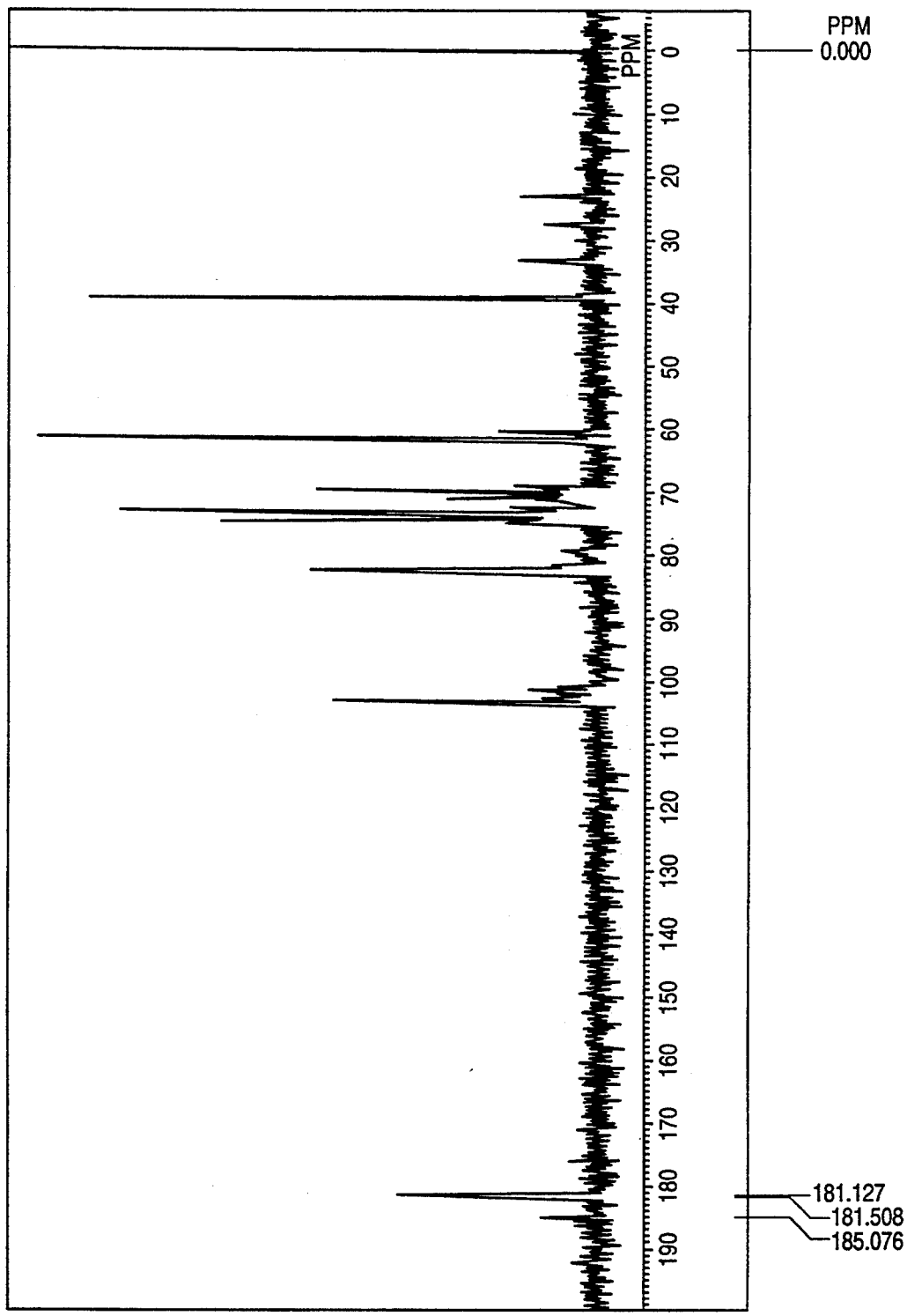
FIG. 7 shows the $^{13}$C-NMR (270 MHz, D$_2$O) spectra (ppm) of the 6-O-(2-carboxyethyl)-$\beta$-cyclodextrin Na salt and 6,6-di-O-(2-carboxyethyl)-$\beta$-cyclodextrin Na salt obtained in Example 4.

| Compound | $^{13}$C-NMR | Other characteristic data |
|---|---|---|
| | | [Control: β-cyclodextrin 4 mM, 6-O-α-D-glucosyl-α-(1→4)-α-D-glucosyl-β-cyclodextrin 8 mM] |
| 6-O-(2-carboxy-ethyl)-β-cyclo-dextrin Na salt and 6,6-di-O-(2-carboxyethyl)-β-cyclodextrin Na salt [also referred to as sodium 3-O-(6-cyclomalto | Na salt: $^{13}$C-NMR (270 MHz, $D_2O$) δ ppm: The spectrum is shown in FIG. 7. Carboxyl-C signal at 181.127, 181.508 and 185.076 ppm | |

TABLE 2-continued

List of Reaction Products

Figure 8:
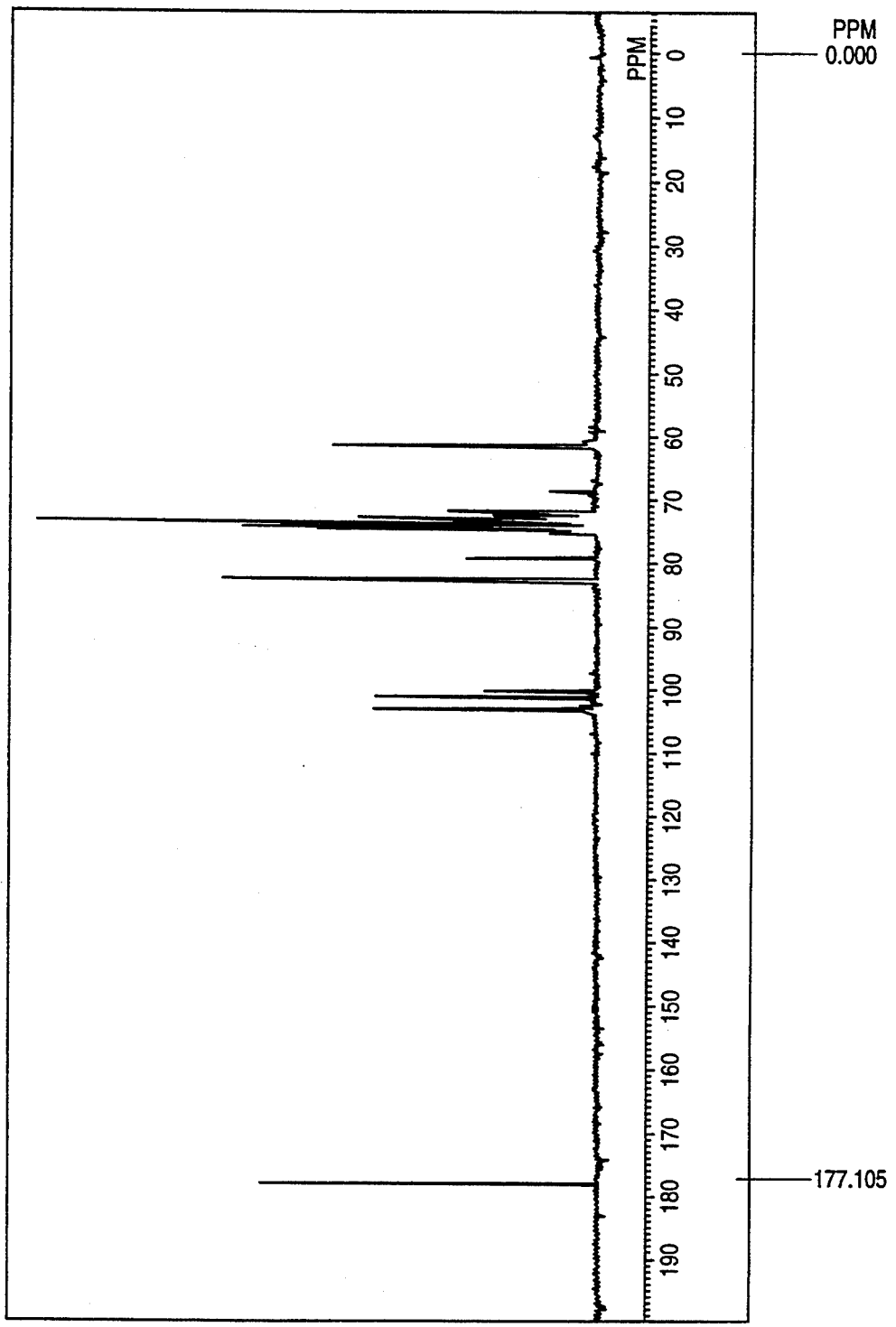
FIG. 8 shows the $^{13}$C-NMR (270 MHz, D$_2$O) spectrum (ppm) of the 6-O-$\alpha$-D-glucuronyl-(14)-$\alpha$-D-glucosyl-$\alpha$-cyclodextrin obtained in Example 4.

| Compound | $^{13}$C-NMR | Other characteristic data |
|---|---|---|
| heptaosyl)-propiohate] (6-O-(3-hydroxy-propyl)-β-cyclo-dextrin and 6,6-di-O-(3-hydroxy-propyl)-β-cyclo-dextrin) | | |
| 6-O-D-glucuronyl-(1→4)-α-D-glucosyl-α-cyclodextrin Na salt [also referred to as sodium 6-D-cyclomaltohexaosy 1-(6→1)-D-α-glucosyl-(4→1)-O-α-D-glucuronate] (6-O-α-maltosyl-α-cyclodextrin) | Na salt: $^{13}$C-NMR (270 MHz, D$_2$O) δ ppm: The spectrum is shown in FIG. 8. Carboxyl-C signal at 177.105 ppm | |

TABLE 3

List of Reaction Products

Figure 9:
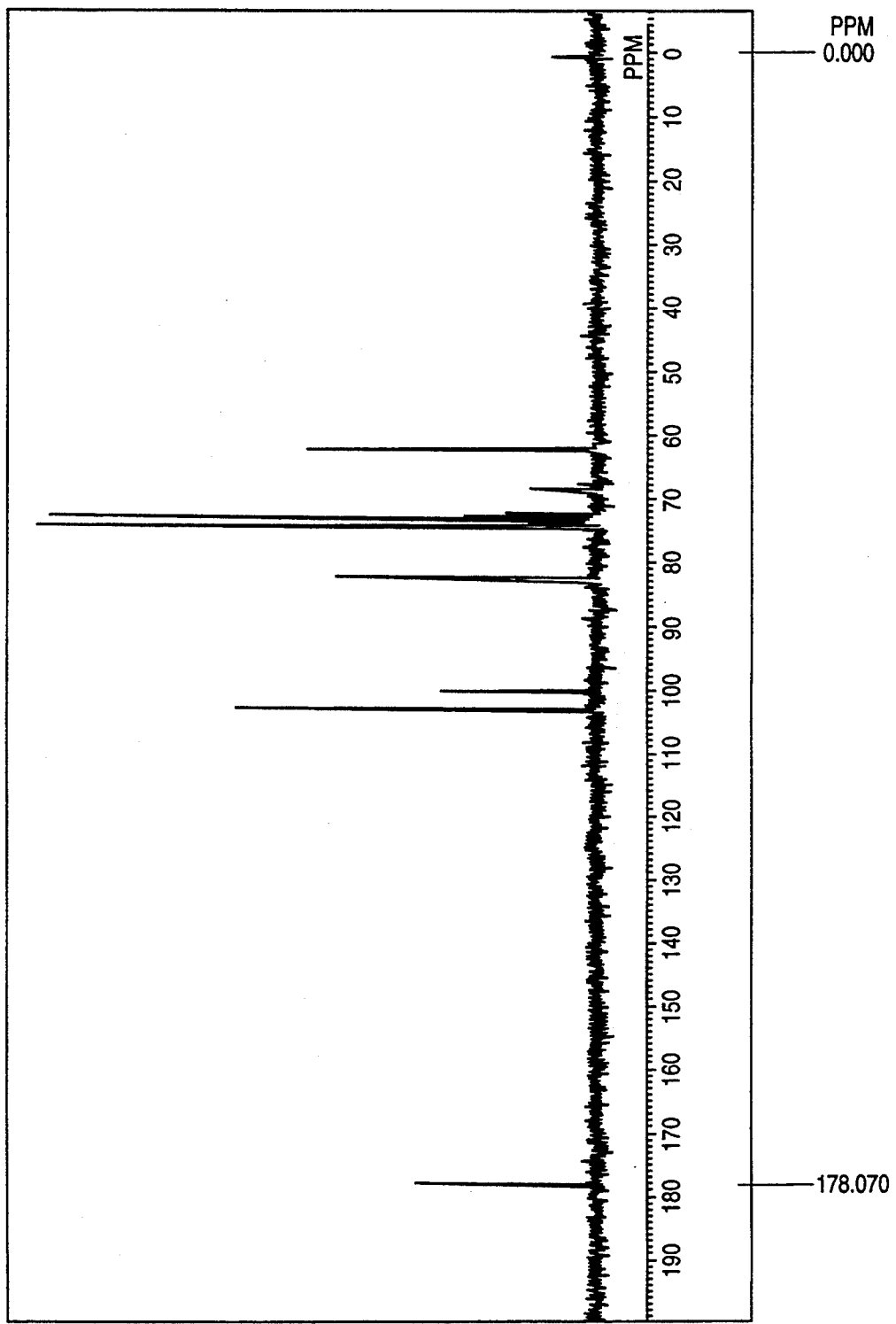
FIG. 9 shows the $^{13}$C-NMR (270 MHz, D$_2$O) spectrum (ppm) of the 6-α-D-glucuronyl-β-cyclodextrin obtained in Example 4.
Figure 10:
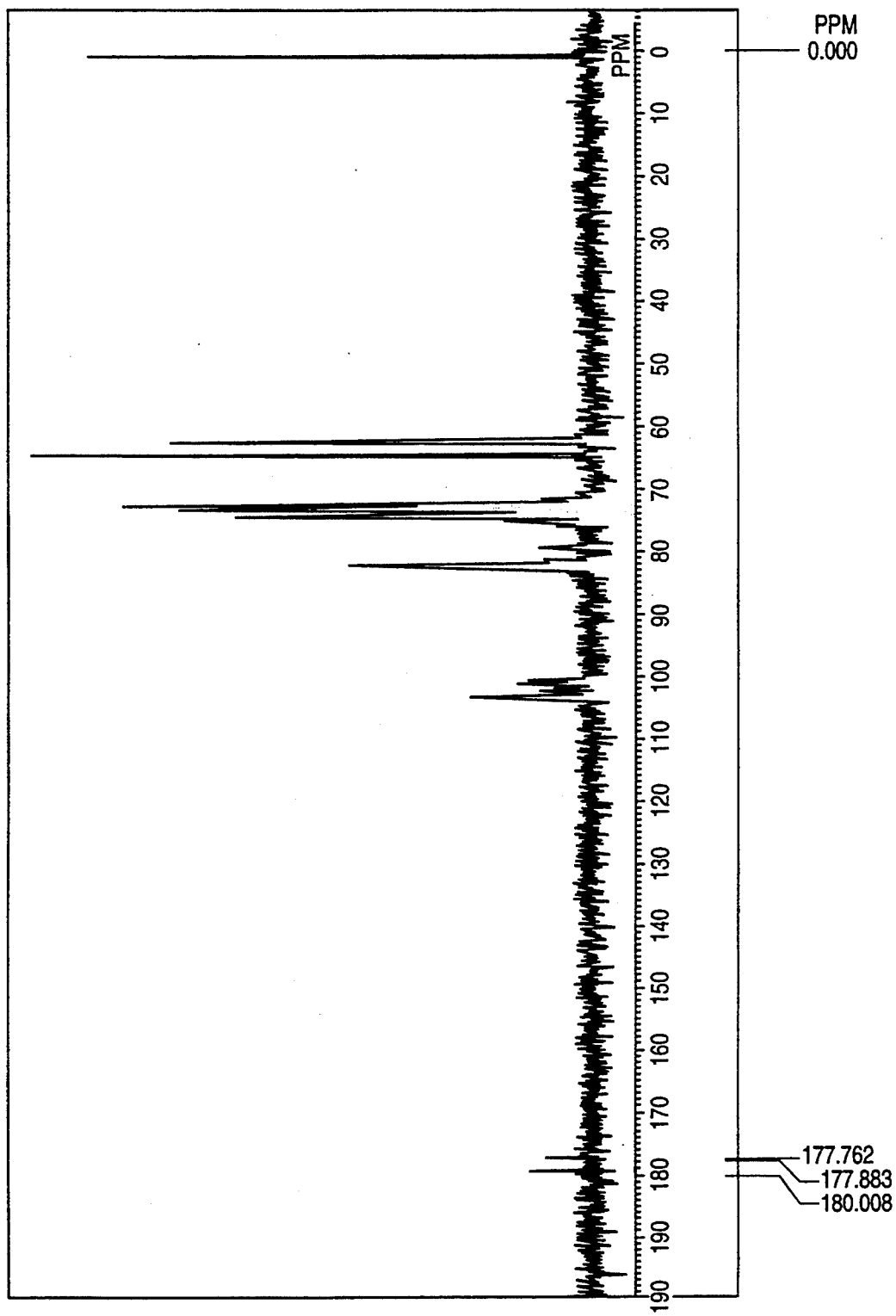
FIG. 10 shows the $^{13}$C-NMR (270 MHz, D$_2$O) spectra (δppm) of 6-O-(2-carboxy-2-hydroxyethyl)-β-cyclodextrin Na salt and 6,6-di-O-(2-carboxy-2-hydroxyethyl)-β-cyclodextrin Na salt obtained in Example 4.
Figure 11:
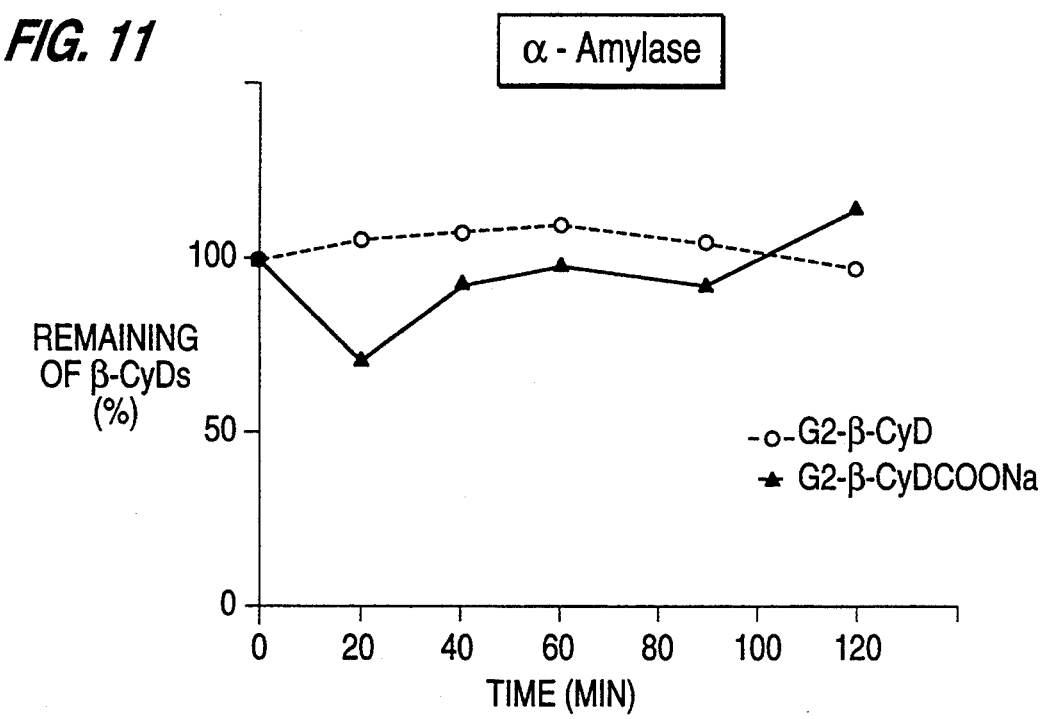
FIG. 11 shows the results of stability assays (time courses of % residues) of 6-O-α-D-glucuronyl(1→4)-α-D-glucosyl-β-cyclodextrin Na salt (legend: G2-β-CyDCOONa) and control 6-O-α-maltosyl-β-cyclodextrin (legend: G2-β-CyD) using α-amylase.
Figure 12:
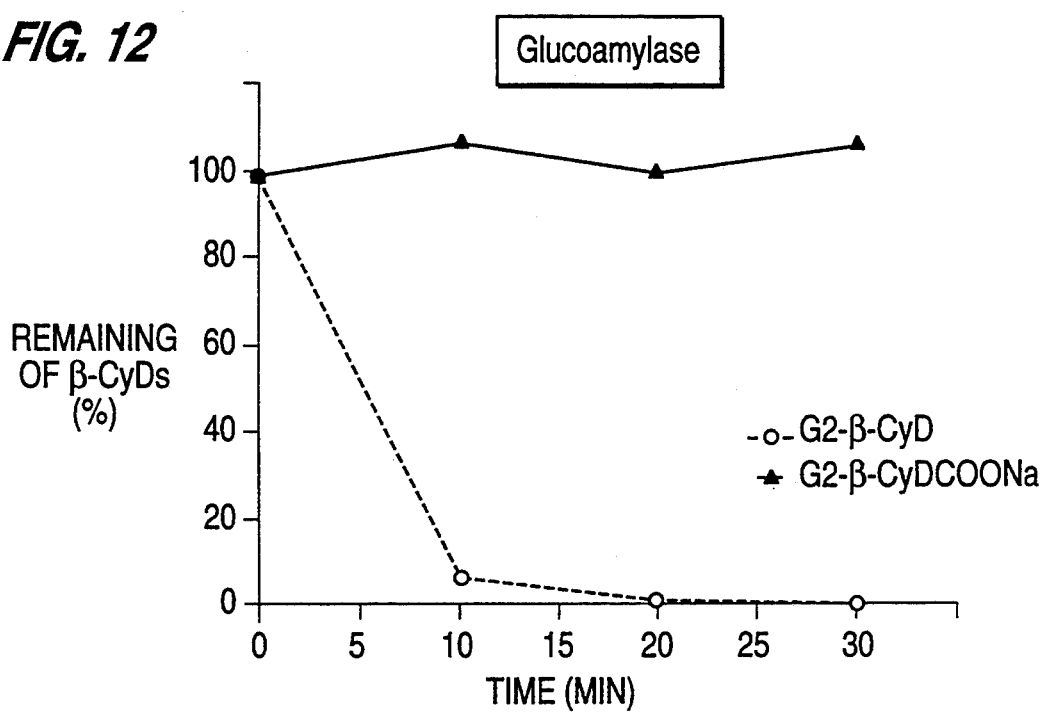
FIG. 12 shows the results of stability assays (time courses of % residues) of 6-O-α-D-glucuronyl(1→4)-α-D-glucosyl-β-cyclodextrin Na salt (legend: G2-β-CyDCOONa) and control 6-O-α-maltosyl-β-cyclodextrin (legend: G2-β-CyD) using glucoamylase.
Figure 13:
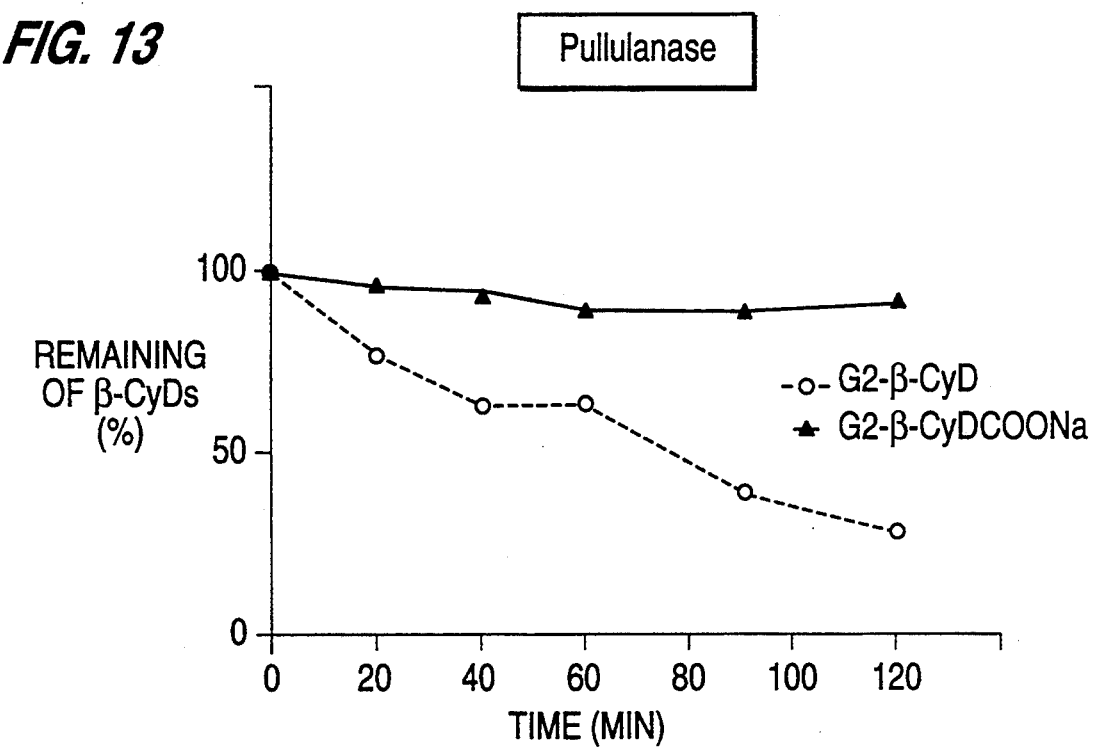
FIG. 13 shows the results of stability assays (time courses of % residues) of 6-O-α-D-glucuronyl(1→4)-α-D-glucosyl-β-cyclodextrin Na salt (legend: G2-β-CyDCOONa) and control 6-O-α-maltosyl-β-cyclodextrin (legend: G2-β-CyD) using pullulanase.
Figure 14:
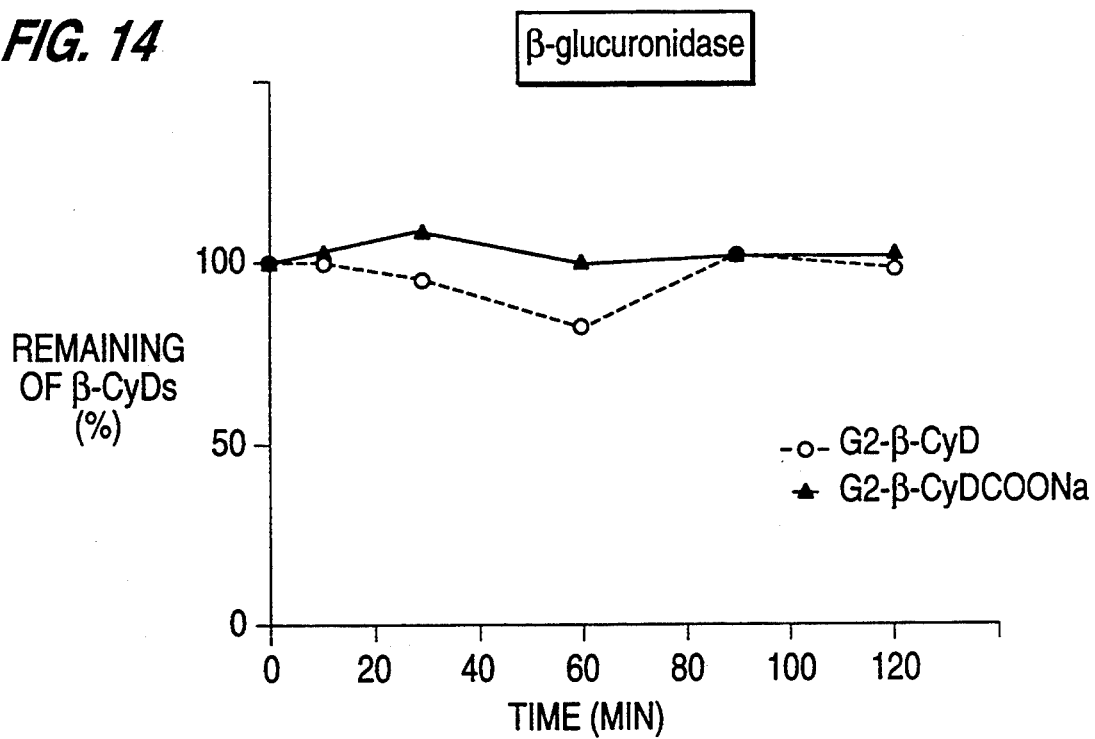
FIG. 14 shows the results of stability assays (time courses of % residues) of 6-O-α-D-glucuronyl(1→4)-α-D-glucosyl-β-cyclodextrin Na salt (legend: G2-β-CyDCOONa) and control 6-O-α-maltosyl-β-cyclodextrin (legend: G2-β-CyD) using β-glucuronidase.

| Compound | Analytical Data |
|---|---|
| 6-O-α-[D-Glucuronyl]-β-cyclodextrin [also referred to as 6-O-cyclomaltoheptaosyl-(6→1)-D-α-glucuronic acid] (6-O-α-D-Glucosyl)-β-cyclodextrin) | TLC: Silica gel, Merck Kiesel Gel 60 (F$_{254}$ No 5715) Solvent system: 1-Propanol-ethyl acetate-H$_2$O acetic acid (6:4:2:4) Yield 64% Rf = 0.25, $^{13}$C-NMR (270 MHz, D$_2$O δ ppm: The spectrum is shown in FIG. 9: the carboxyl-C signal at 178.070 ppm |
| 6-O-α-D-[Glucuronyl-(1→4)-α-D-glucosyl]-α-cyclodextrin [also referred to as 6-O-cyclomaltohexaosyl-(6→1)-D-α-glucosyl-(4→1)-O-α-D-glucuronic acid] (6-O-Maltosyl-α-cyclodextrin) | HPLC: Column, NH2P-50 Mobile phase: Acetonitrile-H$_2$O = 55:45 Flow rate: 1 ml/min Yield 68% Temperature: 25° C. RT = 7.58 |
| 6-O-(2-Carboxy-2-hydroxyethyl)-β-cyclodextrin Na salt [also referred to as sodium 2-hydroxy-3-O-(6-cyclomaltoheptaosyl)-propionate] and 6,6-di-O-(2-carboxy-2-hydroxy-ethyl)-β-cyclodextrin Na salt [also referred to as sodium 7$^A$, 7$^C$-di-O-[α-D-glucuronyl-(1→4)-O-D-glucosyl]-α-(1→6)-maltoheptaose] (6-O-(2,3-Di-hydroxy-propyl)-β-cyclodextrin and 6,6-di-O-(2,3-di-hydroxypropyl)-β-cyclo-dextrin) | $^{13}$C-NMR (270 MHz, D$_2$O) δ ppm: The spectrum is shown in FIG. 10. |

TABLE 4

List of Reaction Products

| Compound | Analytical Data |
|---|---|
| α-D-Glucuronyl-(1→1)-α-D-glucuronic | TLC: Cellulose, Merck HPTLC No. 5876 Solvent system: Phenol-formic acid-H$_2$O (75:10:25) |

TABLE 4-continued

List of Reaction Products

| Compound | Analytical Data |
|---|---|
| acid (D-trehalose) | Color reagent: Alkaline silver nitrate, Rf = 0.32<br>HPLC: Column: Shimadzu SCR 101H<br>Eluent: pH = 2, 0.008SN $H_2SO_4$, flow rate 0.8 ml/min.,<br>25° C., detection by RI & UV RT-6.83 (min) |
| 2-Amino-2-deoxy-D-glucuronic acid (D-glucosamine) | TLC: Cellulose, Merck HPTLC No. 5876<br>Solvent system: Phenol-formic acid $H_2O$ (75:10:25)<br>Color reaction with ninhydrin reagent, Rf = 0.39 |
| 13-O-$\beta$-D-Glucosyl-(1→2)-D-glucosyl-19-$\beta$-D-glucuronyl-steviol (stevia extract) | TLC: Silica gel, Merck Kiesel Gel 60 ($F_{254}$ No. 5715)<br>Solvent system: $CHCl_3$—MeOH—$H_2O$ (6:4:1)<br>Color reaction: Sulfuric acid-MeOH (1:1), 110-120°,<br>10 min., heating, Rf = 2.6 |
| 5'-Carboxyinosine (inosine) | TLC: Cellulose, Merck HPTLC No. 5876<br>Solvent system: $H_2O$, detection: UV, Rf = 0.95<br>(Reference: inosine Rf = 0.77) |
| 1-Carboxy-2,7-anhydro-$\beta$-D-altroheptulose (2,7-anhydro-$\beta$-D-altroheptulose) | HPLC: Column, Shimadhu SCR 101H,<br>Solvent system: pH = 2; 0.008N-$H_2SO_4$, flow rate 0.8<br>ml/min., temperature 25° C., detection by RI, UV<br>RT = 14.24 (min.)<br>(Reference: heptulose RT = 20.14) |
| Validamycin A oxide [R=COOH in formula (II)] (Validamycin A) | HPLC: Column Asahi Pak GS 320, 35° C. solvent<br>0.008$NH_2SO_4$, flow rate 1 ml/min., detection by RI,<br>RT = 13.55 (Reference: validamycin A (R = $CH_2OH$),<br>RT = 12.68)<br>TLC: Silica gel plate,<br>Solvent system: n-Butanol-ethanol-$H_2O$-pyridine<br>(35:15:40:10),<br>Color reaction with naphthoresorcin-sulfuric acid,<br>RF = 0.56 |

EXAMPLE 5

A Biot's 5-liter jar fermentor was charged with 1 l of the same cell suspension of *Pseudogluconobacter saccharoketogenes* as described in Example 1 and 30 g of a stevia extract (steviol glycoside composed mainly of stevioside) followed by addition of 1 l of sterilized water. While this reaction system was agitated at 800 rpm (32° C.) under aeration at 1.6 l/min., 10% NaOH solution was added dropwise automatically to control the reaction system at pH 6.3 throughout the reaction. The substrate disappeared in 1.5 hours, whereupon the reaction is stopped. The reaction mixture, 2 liters, was refrigeration-centrifuged at 8000 rpm to remove the cells and the supernatant was passed through an HP-2 (aromatic synthetic adsorbent, Mitsubishi Kasei) column (1.8 l). The column was washed with $H_2O$, (8 l) and elution was carried out with 50% EtOH (5 l). This eluate provided glucuronic acid type steviol glycosides in mixture. The eluate was concentrated and lyophilized to provide 19.2 g of white powder. This product had an intense, savory sweet taste.

The above product was subjected to HPLC under the following conditions.
HPLC column: ODP
Eluent: $CH_3CN$—$H_2O$=3:7, supplemented with 0.1% of trifluoroacetic acid
Flow rate: 1.0 ml/min.
Temperature: 35° C.
Detector: RI and UV
The HPLC pattern (RI detection) is shown in FIG. 1.
TLC plate: silica gel, Merck Kieselgel 60 $F_{254}$ No. 5715
Solvent system: $CHCl_3$:MeOH:$H_2O$ (6:4:1)
Color reagent: Sulfuric acid-MeOH (1:1)
Temperature: heating at 110°-120° C. for 10 min.
Rf=2.6
The $^{13}C$-NMR ($D_2O$) spectrum of this product showed chemical shifts assignable to carbonyl-carbon at 177.87 (ester) and 171.84 (COO−), indicating the generation of carboxyl groups. The HPLC pattern indicated that this product was mostly composed of the compound formed as the glucose attached to the $C_{19}$-position and that attached to the $C_{13}$-position of stevioside had been converted to uronic acids.

EXAMPLE 6

Figure 2:
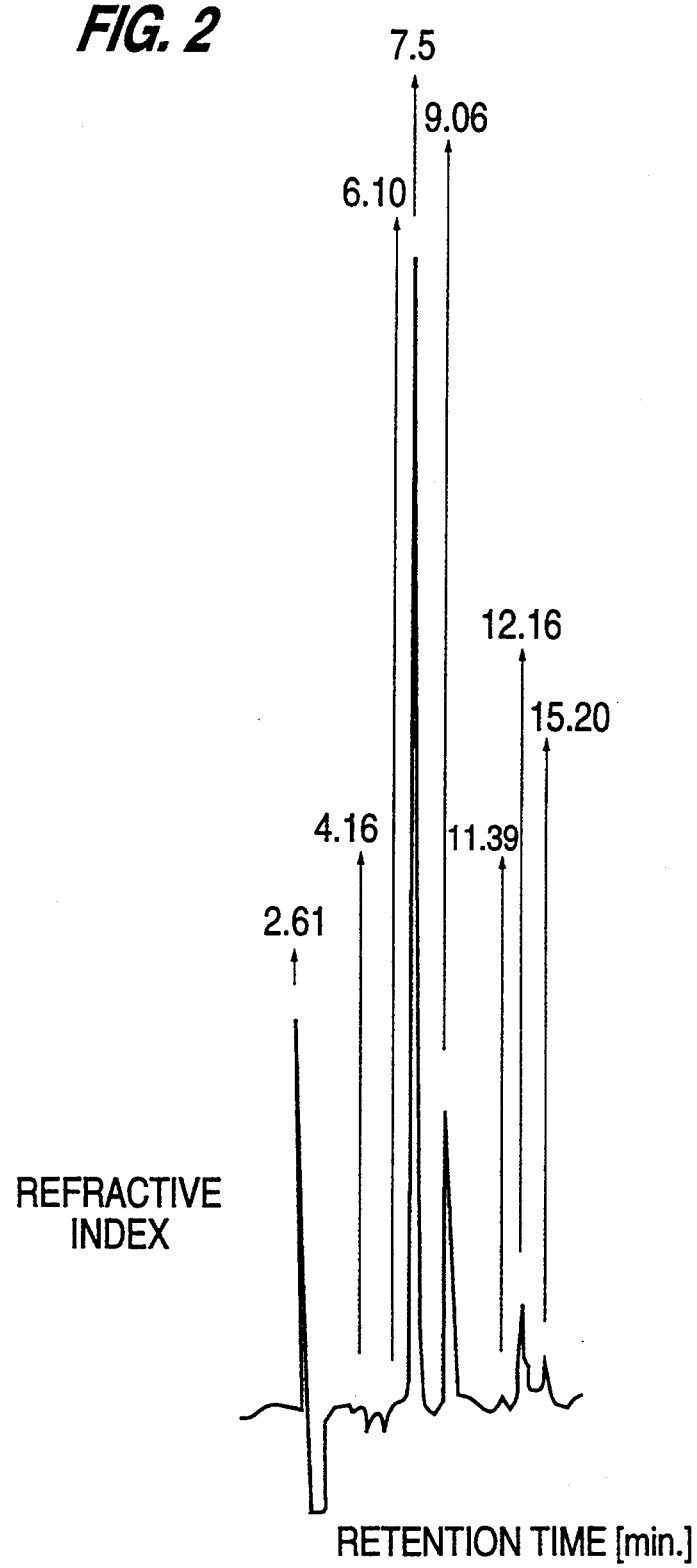
FIG. 2 shows the HPLC pattern (RI detection) of the glucuronic acid type steviol glycoside obtained in Example 6.

In the same manner as Example 5, 30 g of a stevia extract (steviol glycosides composed mostly of stevioside) was oxidized using 1 l of a cell suspension of *Pseudogluconobacter saccharoketogenes* at 32° C. under agitation at 800 rpm and sparging with air at 1.6 l/min and the reaction was stopped when 59 ml of 5% NaOH (corresponding to about 2 equivalents of oxidation) had been added dropwise. The necessary oxidation time was 21 hours. The reaction mixture was then centrifuged to remove the cells and the supernatant (1850 ml) was purified (as in Example 5) to provide 13.0 g of glucuronic acid type steviol glycoside Na salts in mixture as white powder. This product had an intense yet sumptuous sweet taste.
HPLC: column ODP, temperature 35° C.
Mobile phase: $CH_3CN$—$H_2O$=3:7 supplemented with 0.1% trifluoroacetic acid
Flow rate: 1 ml/min.
The HPLC pattern (RI detection) is shown in FIG. 2.

EXAMPLE 7

Stevioside, 30 g, was oxidized with *Pseudogluconobacter saccharoketogenes* in the same manner as in Example 5. The reaction consumed 30ml of 5% sodium hydroxide in 90 minutes. The reaction mixture was purified to provide 20 g of white powder. This product showed an intense yet sumptuous sweet taste.

Figure 3:
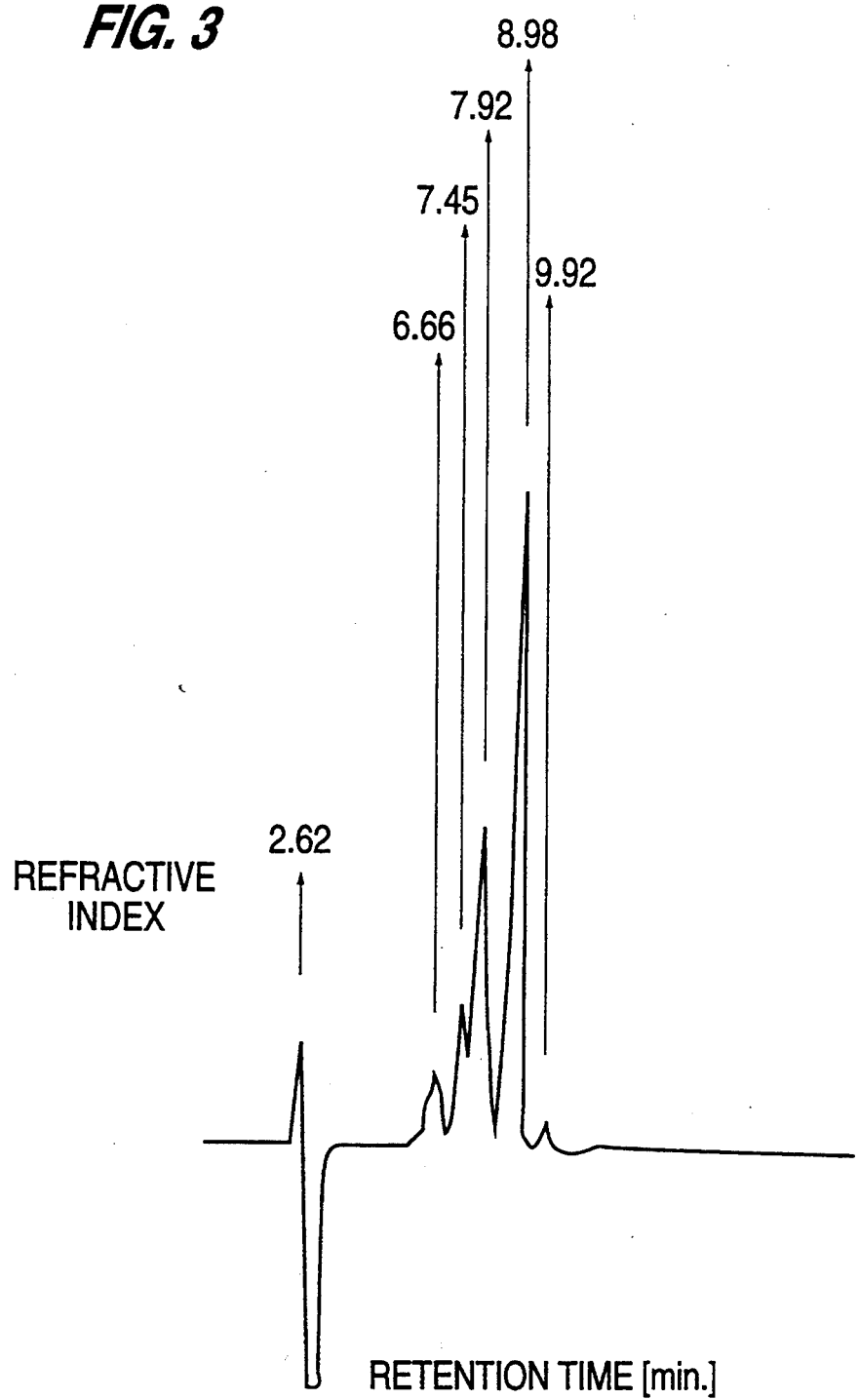
FIG. 3 shows the HPLC pattern (RI detection) of the glucuronic acid type stevioside sodium salt obtained in Example 7.

The HPLC pattern (RI detection) of the above product is shown in FIG. 3. This white powder, 400 mg, was purified using a reversed phase ODP-50 column (o/21.5×300 mm, Asahi Kasei) and water-acetonirile (72:28) supplemented with 0.1% trifluoroacetic acid and the main fraction was concentrated and lyophilized to provide 124 mg of white powder. This product was recrystallized from methanol-water (9:1) to provide colorless needles, m.p. 226°–230° C. (decomp.).

IR (KBr) cm$^{-1}$: 3500-3250, 1715, 1605, 1080-1010, 890.

| assignment | $\delta_H$ ppm | $\delta_C$ ppm |
| --- | --- | --- |
| 1 | 0.86, 1.91 | 43.13 |
| 2 | 1.47, 1.88 | 21.54 |
| 3 | 1.09, 2.19 | 40.23 |
| 4 | — | 46.67 |
| 5 | 1.15 | 59.74 |
| 6 | 1.90 | 24.15 |
| 7 | 1.44, 1.62 | 43.73 |
| 8 | — | 44.72 |
| 9 | 1.00 | 56.31 |
| 10 | — | 42.03 |
| 11 | 1.64, 1.85 | 23.03 |
| 12 | 1.56, 1.99 | 39.06 |
| 13 | | 89.79 |
| 14 | 1.49, 2.22 | 46.95 |
| 15 | 2.05, 2.22 | 49.86 |
| 16 | — | 156.08 |
| 17 | 4.94, 5.17 | 107.45 |
| 18 | 1.27 | 30.86 |
| 19 | — | 181.50 |
| 20 | 0.92 | 17.97 |
| 1' | 4.73 | 98.62 |
| 2' | 3.55 | 83.48 |
| 3' | 3.68 | 79.14 |
| 4' | 3.44 | 72.54 |
| 5' | 3.35 | 78.45 |
| 6' | 3.73, 3.87 | 63.58 |
| 1" | 4.71 | 105.89 |
| 2" | 3.33 | 77.11 |
| 3" | 3.51 | 78.52 |
| 4" | 3.34 | 72.73 |
| 5" | 3.41 | 79.11 |
| 6" | 3.68, 3.88 | 64.14 |
| a | 5.45 | 96.67 |
| b | 3.56 | 74.63 |
| c | 3.57 | 78.72 |
| d | 3.56 | 74.36 |
| e | 3.83 | 79.27 |
| f | — | 177.73 |

Elemental analysis for $C_{38}H_{57}O_{19}Na \cdot 1.5H_2O$
Calcd.: C, 52.59; H, 6.97
Found: C, 52.56; H, 7.15

Based on the above data, the main oxidation product obtained was the sodium salt of compound (II) wherein $R_1 = -\beta$-Glc-2-$\beta$-Glc, $R_2 = -\beta$-Glc UA, namely 13-O-$\beta$-sophorosyl, 19-O-$\beta$-D-glucuronylsteviol sodium salt of the following formula (IV).

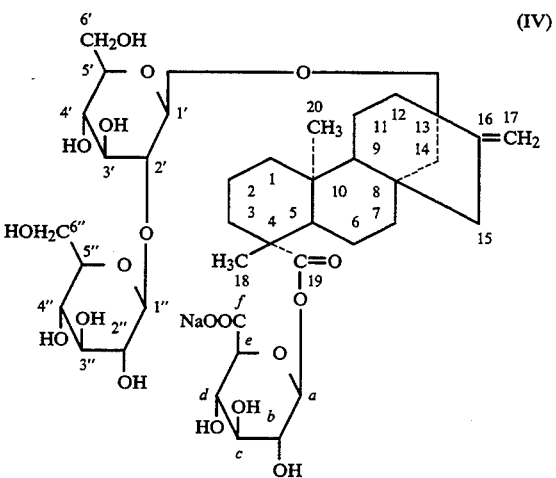

EXAMPLE 8

Figure 4:
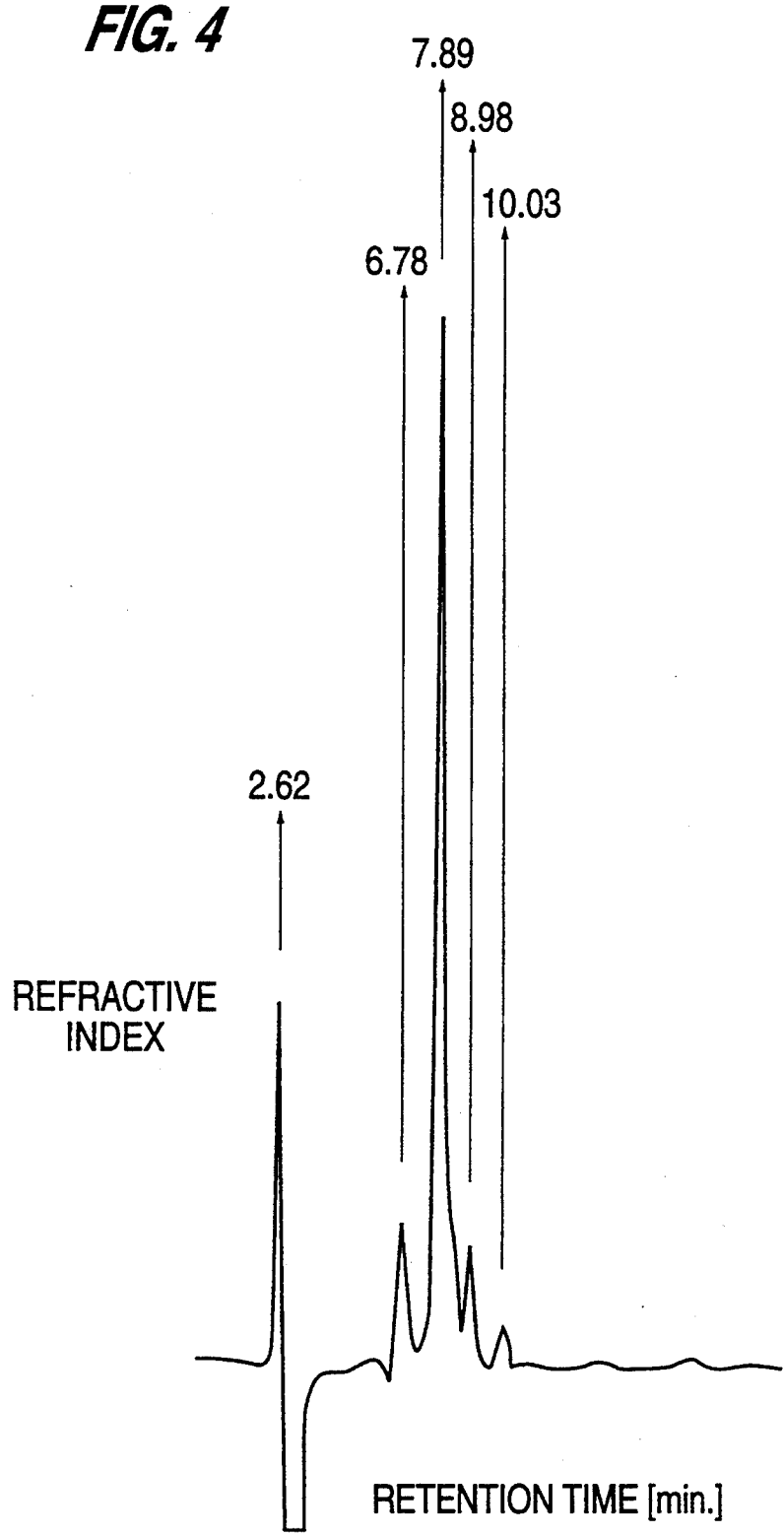
FIG. 4 shows the HPLC pattern (RI detection) of the glucuronic acid type stevioside disodium salt obtained in Example 8.

Stevioside, 30 g, was oxidized with *Pseudogluconobacter saccharoketogenes* as in Example 5. The reaction consumed 67 ml of 5% sodium hydroxide in 80 minutes. The reaction mixture was then purified to provide 32 g of white powder. This product has an intense yet sumptuous sweet taste. The HPLC pattern (RI detection) of this product is shown in FIG. 4. By Subjecting 1 g of this white powder to HPLC using a reversed phase ODP-50 column (o/21.5×300 mm, Asahi Kasei) and a gradient series of 2% acetic acid/acetonitrile, 0.22 g of a main oxidation product was obtained. The secondary ion mass spectrometry (SI-MS) of this product showed a peak at m/z 869 (M+2H$_2$O.H$^+$).

$^{13}$C-NMR (d$_6$-pyridine) ppm: 15.12, 18.95, 20.21, 21.69, 27.78, 37.91, 37.96, 39.33, 39.41, 40.35, 42.12, 43.58, 43.91, 47.23, 53.55, 56.86, 62.57, 70.07, 71.54, 72.49, 72.75, 75.75, 76.16, 76.79, 76.83, 77.51, 77.72, 77.78, 86.00, 86.97, 95.07, 97.60, 103.89, 103.94, 153.50, 171.26, 171.89, 176.23.

Based on the above data, this product was identified to be the disodium salt of compound (II) wherein $R_1 = -\beta$-Glc-2-$\beta$-GlcUA and $R_2 = -\beta$-Glc UA, namely 13-O-[2-O-($\beta$-glucuronyl)]-$\beta$-D-glucosyl, 19-O-$\beta$-D-glucuronylsteviol disodium of the following formula (V).

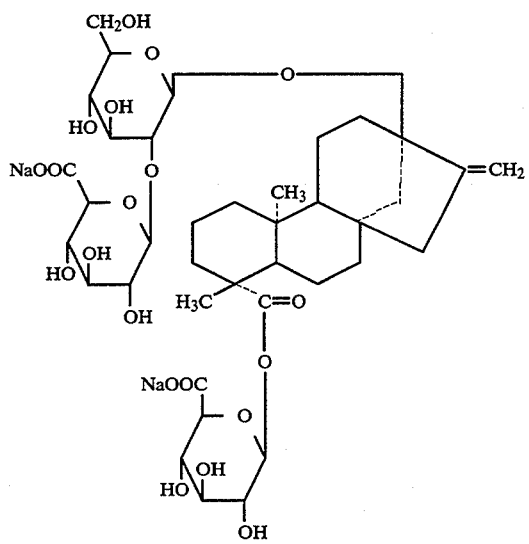

(V)

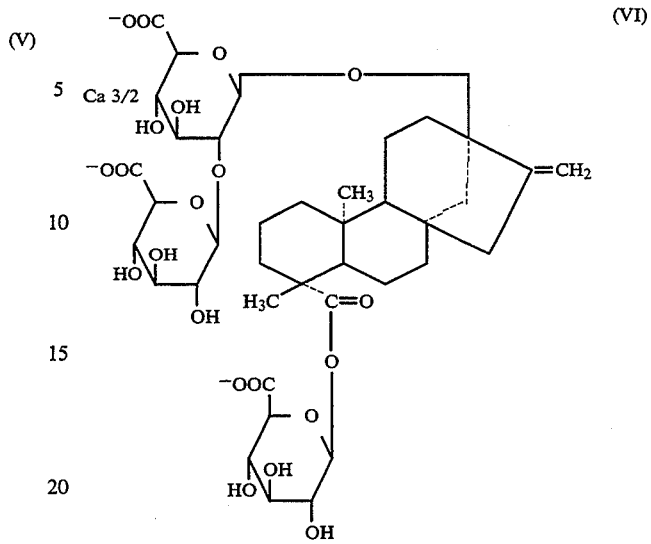

(VI)

EXAMPLE 9

As in Example 5, a Biot's 5-liter jar fermentor was charged with 30 g of stevioside followed by addition of 1.6 l of sterilized water. While this reaction system was stirred at 800 rpm (32° C.) and air was bubbled at the rate of 1 l/min, 20 g of calcium carbonate was added and the reaction was carried out for 4 hours. The reaction mixture, 2 l, was then centrifuged at 8000 rpm to remove the cells and the supernatant was passed through a column (1.8 l) of HP-20 (aromatic synthetic absorbent, Mitsubishi Kasei). The column was washed with $H_2O$ (8 l) and elution was carried out with 50% ethanol (5 l). The eluate contained uronic acid type stevioside calcium salt. This product was concentrated and lyophilized to provide 12.98 g of white powder. This powder was recrystallized from methanol to provide colorless needles. This product had a mildly sweet taste.

$^{13}C$-NMR ($d_6$-pyridine) ppm: 15.93, 19.74, 20.92, 21.00, 28.58, 38.66, 38.71, 40.06, 41.04, 41.86, 42.00, 42.91, 44.33, 48.19, 54.50, 57.63, 73.11, 73.30, 73.45, 73.97, 74.08, 76.53, 77.72, 77.86, 77.89, 78.34, 78.39, 84.79, 86.79, 95.84, 98.21, 105.46, 107.02, 153.70, 171.93, 172.18, 172.95, 176.78.

Based on the above data, this product was identified to be the calcium salt of compound (II) wherein $R_1 = -\beta$-Glc UA-2-$\beta$-GlcUA, $R_2 = -\beta$-GlcUA, namely 13-O-[2-O-$\beta$-glucuronyl]-$\beta$-D-glucuronyl, 19-O-$\beta$-D-glucuronylsteviol calcium salt of the following formula (VI):

EXAMPLE 10

As in Example 5, 15.8 g of cells of *Pseudogluconobacter saccharoketogenes* and 2000 ml of sterilized water were added to 10 g of substrate rebaudioside A and the reaction was carried out at 32° C. with stirring at 800 rpm under aeration at 1.6 l/min. The reaction system was controlled at pH 6.3 with 2% NaOH solution. When 3 ml of 2% NaOH had been consumed, the reaction was stopped and the reaction mixture was centrifuged to obtained the supernatant. The reaction time was 135 minutes. The supernatant was purified as in Example 5 to provide 10.16 g of white powder.

Figure 5:
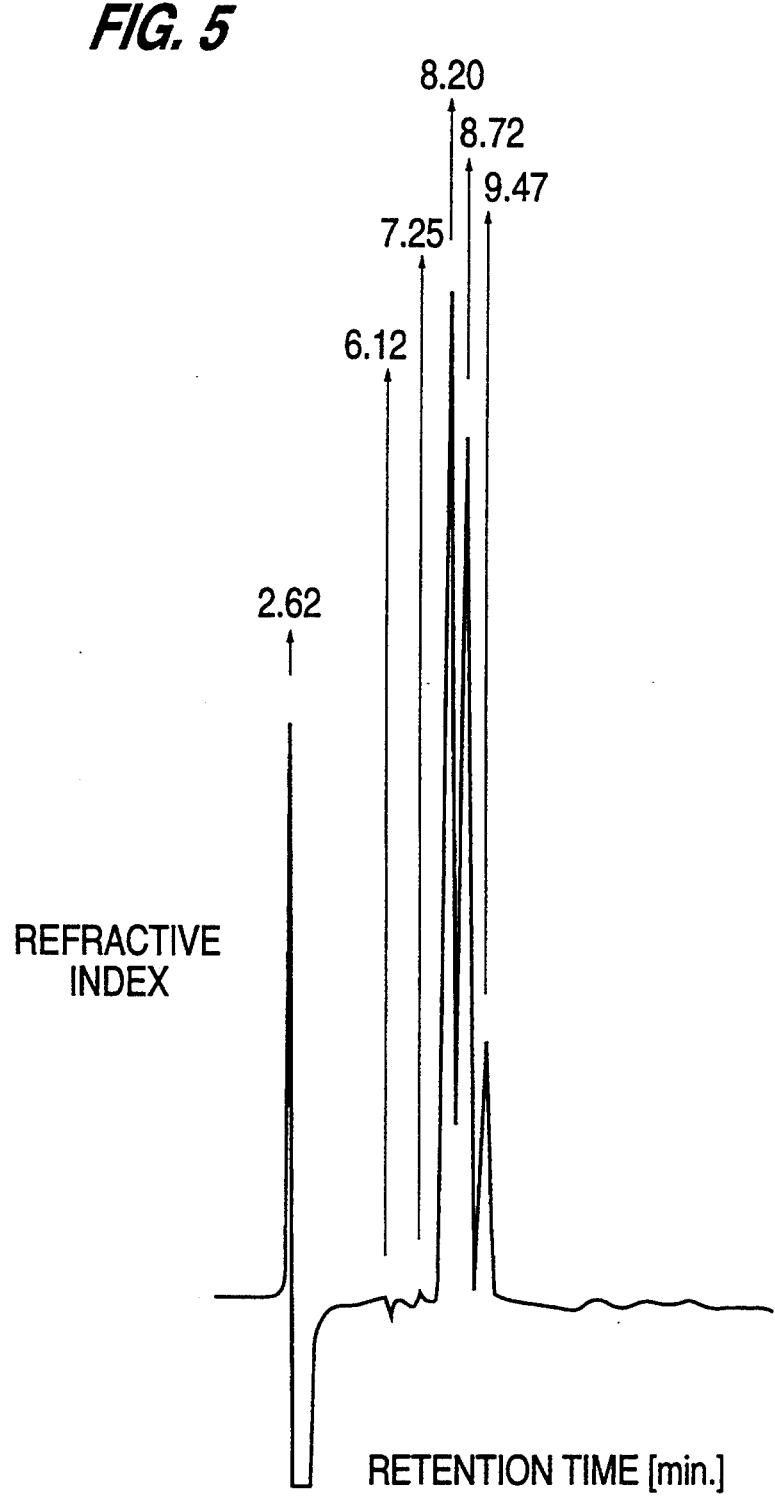
FIG. 5 shows the HPLC pattern (RI detection) of one-equivalent oxidation product of rebaudioside A as obtained in Example 10.

The HPLC pattern (RI detection) of this product is shown in FIG. 5.

IR (KBr)cm$^{-1}$:3340, 1720, 1610, 1410, 1070.

This product had an intense yet sumptuous taste.

EXAMPLE 11

A Biot's 5-liter jar fermentor was charged with 1 liter of the same cell suspension of *Pseudogluconobacter saccharoketogenes* as used in Example 1 and 30 g of stevioside, followed by addition of 1 l of sterilized water and 200 ml of Amberbite IRA-68 (hereinafter referred to briefly as IRA-68) to provide a reaction system. While this system was stirred at 800 rpm (32° C.), air was bubbled through the system at 1.6 l/min. As the supernatant fluid ceased to show stevioside in 2 hours, the reaction was stopped and the mixture was centrifuged to separate IRA-68. The IRA-68 was filled into a column (o/4×24 cm) and elution was carried out with 2 l of 2N-NaCl. The eluate was passed through an HP-20 column (0.5 l). The column was washed with 1 l of water and elution was carried out with 0.8 l of 50% MeOH-$H_2O$. The eluate was concentrated to dryness to provide 9.20 g of white powder. This powder was recrystallized from methoanol-water (9:1) to provide colorless needles; m.p. 226°–230° C. (decomp.)

This product was identified to be 13-O-$\beta$-sophorosyl-19-O-$\beta$-glucuronylsteviol sodium salt (IV) shown in Example 7.

EXAMPLE 12

As in Example 11, a Biot's 5-liter jar fermentor was charged with 1 l of a cell suspension of *Pseudo-*

Figure 6:
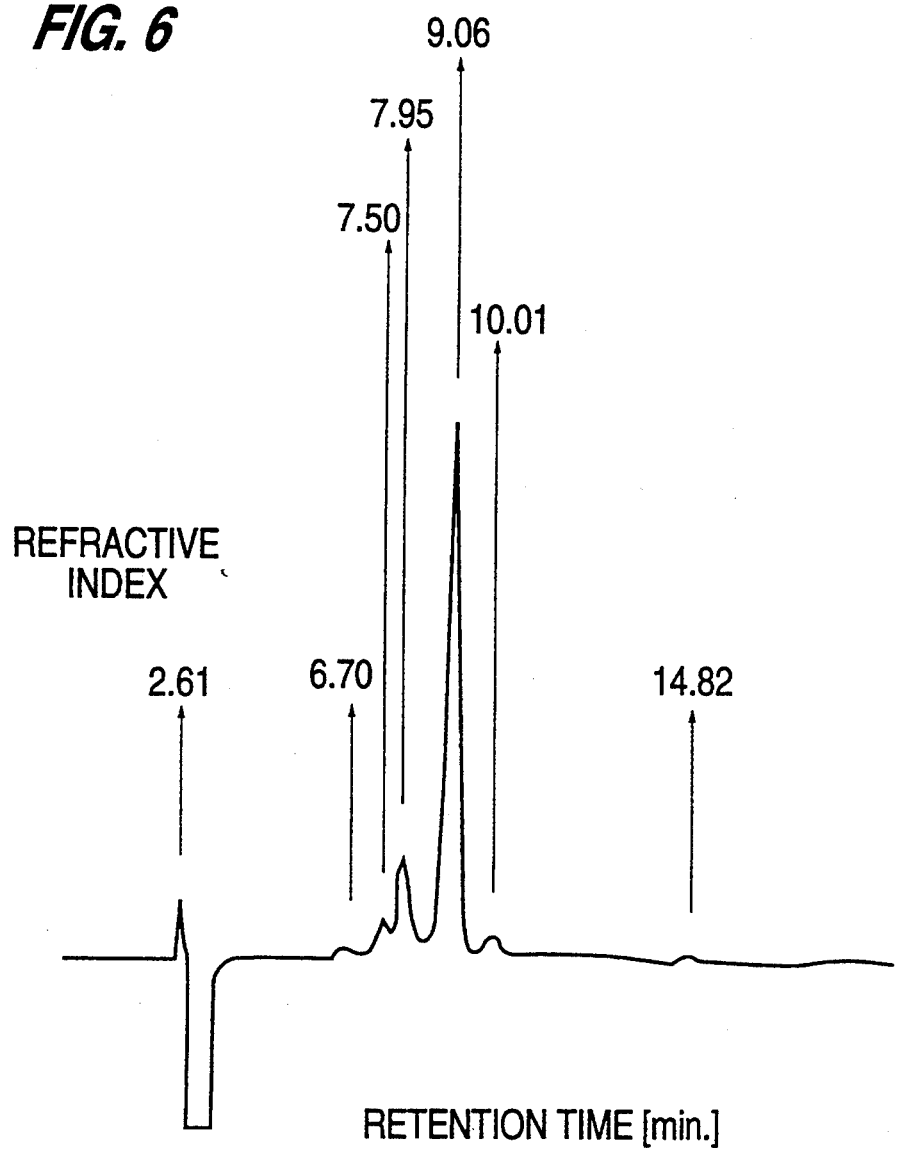
FIG. 6 shows the HPLC pattern (RI detection) of the glucuronic acid steviol glycosides in mixture obtained in Example 12.

*gluconobacter saccharoketogenes* and 30 g of a stevia extract (a mixture of at least 6 different steviol glycosides) followed by addition of 1 l of sterilized water and 200 ml of IRA-68. While this reaction system was stirred at 800 rpm (32° C.), air was introduced at the rate of 1.6 l/min. As the supernatant fluid ceased to show stevioside in 2 hours, the reaction was stopped and the reaction mixture was centrifuged to separate IRA-68 from the supernatant. The IRA-68 was filled into a column (o/4×25 cm) and elution was carried out with 1 l of 2N-NaCl. The eluate was passed through an HP-20 column (0.5 l). The column was washed with 1 l of water and elution was then carried out with 1 l of 50% MeOH-H$_2$O. The eluate thus obtained was concentrated to dryness to provide 8.9 g of white powder. The HPLC pattern,(RI detection) of this product is shown in FIG. 6.

IR (KBr) cm$^{-1}$: 3500-3200, 1720, 1705, 1610, 1400

EXAMPLE 13

A transglycosylated glycoside (SK Sweet, Sanyo Kokusaku Pulp Co.), 30 g, was oxidized and purified in the same manner as in Example 6 to provide 28.3 g of white powder. The $^{13}$C-NMR spectrum (D$_2$O) of this product showed 8 signals (179.50, 179.46, 179.40, 179.37, 179.32, 179.26, 177.10, 177.07 ppm) in the carbonyl-C region, suggesting that at least one primary acid group of the saccharide had been converted to a carboxyl group. This product had a sumptuous sweet taste.

EXAMPLE 14

In the same manner as Example 11, 200 mg of mogroside V, the high-sweetness glycoside occurring in *Momordica grosvenori* was added to a suspension of 10 ml equivalent (0.32 g) of *Pseudogluconobacter saccharoketogenes* in 3 ml of water followed by addition of 5 ml of IRA-68. This mixture was stirred at 229 rpm (30° C.) for 5.5 hours. The reaction mixture was allowed to stand and the supernatant was decanted off. The residual IRA-68 was filled into a column and the column was washed with water (50 ml). Then, elution was carried out with 0.01 N-HCl .The eluate was collected and lyophilized to provide a white powder (32 mg). Based on its IR data [(KBr)cm$^{-1}$ 3300, 1600, 1410, 1060-1000], it was confirmed that the glucose chain had been converted to the uronic acid. This product had a sweet taste resembling that of sucrose.

EXAMPLE 15

In 60 ml of sterilized water was dissolved 1.0 g of rubusoside followed by addition of 13 ml of IRA-68. Then, 30 ml of the cell suspension of *Pseudogluconobacter saccharoketogenes* described in Example 1 was added and the reaction was,carried out at 32° C. with stirring at 600 rpm under aeration at the rate of 60 l/min. for 240 minutes. The IRA-68 was separated from the reaction mixture and filled into a column. The column was rinsed with 15 ml of water and elution was carried out with 200 ml of 2 N-NaCl solution at SV=0.5. The eluate was applied to an HP-20 column (20 ml). The column was washed with 150 ml of water and elution was carried out with 50% MeOH solution (100 ml) at SV=0.5. The eluate was concentrated to dryness and the crystalline residue was recrystallized from methanol to provide 0.48 g of colorless grainy crystals. m.p. 184°-188° C. (decomp.)

Elemental analysis for C$_{32}$H$_{47}$O$_{14}$Na.5H$_2$O
Calcd.: C, 49.99; H, 7.47
Found: C, 50.05; H, 7.54

TABLE

| $^{13}$C-NMR Spectral Data (Solv. D$_2$O) assignment | |
|---|---|
| | δc ppm |
| 1 | 40.16 |
| 2 | 18.43 |
| 3 | 37.24 |
| 4 | 43.14 |
| 5 | 56.37 |
| 6 | 21.08 |
| 7 | 40.93 |
| 8 | 41.44 |
| 9 | 52.97 |
| 10 | 38.80 |
| 11 | 19.84 |
| 12 | 36.58 |
| 13 | 84.83 |
| 14 | 43.42 |
| 15 | 47.12 |
| 16 | 153.02 |
| 17 | 104.03 |
| 18 | 28.02 |
| 19 | 175.75 |
| 20 | 15.16 |
| 1' | 97.83 |
| 2' | 72.36 |
| 3' | 76.39 |
| 4' | 70.43 |
| 5' | 74.32 |
| 6' | 55.93 |
| a | 94.05 |
| b | 71.77 |
| c | 76.96 |
| d | 61.13 |
| e | 73.60 |
| f | 171.82 |

Based on the above data, the product was identified to be the compound of the following formula (VII).

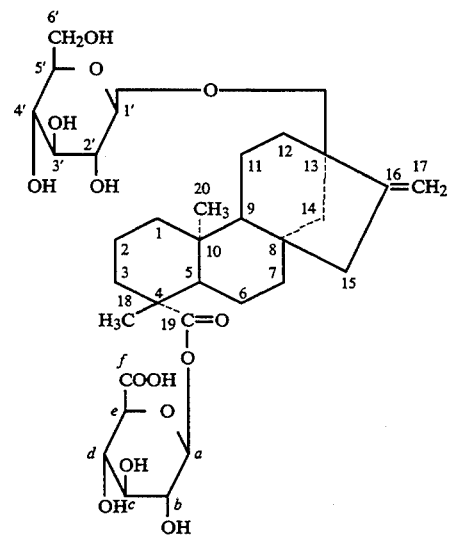

(VII)

This product (VII) was found to be a quality high-sweetener resembling purified sucrose without bitterness.

EXAMPLE 16

| Fursultiamine hydrochloride | 10 mg |
|---|---|
| Vitamin B$_2$ | 2 mg |
| Taulin | 1000 mg |
| Benzoic acid | 30 mg |
| Butyl p-hydroxybenzoate | 2.5 mg |

| | |
|---|---|
| Glucuronic acid-type stevioside sodium salt (IV) | 50 mg |
| Citric acid | 100 mg |
| Glycine | 500 mg |

A drink was produced according to the above formula by the method described below. Thus, butyl p-hydroxybenzoate and benzoic acid were dissolved in about 30 ml of prewarmed water at about 70° C. When the solution had cooled to about 25° C. fursultiamine hydrochloride, vitamin $B_2$, taulin, glucuronic acid-type stevioside (a sweetner), citric acid and glycine were dissolved. The whole solution was adjusted to pH 3.5 with 1 N sodium hydroxide and made up with water to 50 ml.

EXAMPLE 17

First, 30 g of precipitated calcium carbonate, 5 g of magnesium carbonate, 58.5 g of lactose and 6 g of hydroxypropylcellulose were evenly blended and, after 30 ml of water was added, the composition was granulated. The resultant granulation was dried and pulverized. The powder thus obtained was blended with 0.05 g of glucuronic acid type stevioside (a corrigent) and 0.5 g of magnesium stearate and the resultant composition was compression-molded to provide tablets each weighing 200 mg and sized 8.5 mm in diameter.

EXAMPLE 18

A Biot's 5-liter jar fermenter was charged with 1.5 l of the cell suspension of *Pseudogluconobacter saccharoketogenes* described in Example 1, and 30 g of dextran-4 (mol. wt. 4000–6000, Extra Synthese, France) followed by addition of 1.7 l of sterilized water. The reaction was carried out at 32° C. with stirring at 600 rpm under aeration at the rate of 1.6 l/min., with 0.5% NaOH solution being automatically added dropwise so as to maintain the reaction system at pH 6.3 throughout the reaction. The reaction was stopped after 3 hours and the reaction mixture, 12.0 l, was refrigeration-centrifuged at 8000 rpm to remove the cells and provide 1.98 l of supernatant fluid. This supernatant was filtered through a cellulose acetate membrane filter (o/0.2- μm) for further removal of cells. This filtrate was passed through an Amberlite IRA-80 (OH-form) column (50 ml) and the column was washed with a small amount (100 ml) of water to recover 2 l of effluent. This effluent was applied to an HP-20 column (900 ml) and elution was carried out with 2 l of water. The initial 700 ml portion of the eluate was discarded and the succeeding 3.3 l portion was collected. This fraction was acidified with 13.8 ml of concentrated hydrochloric acid and filtered through a cellulose acetate membrane filter (o/0.2 μm). The filtrate was applied to 100 ml of Sepha-beads (tradename) SP205 (Mitsubishi Kasei). The adsorbent was washed with 700 ml of 0.05 M HCl and 2 l of water and elution was carried out with 2 l of 20% MeOH solution to provide the desired fraction. This fraction was concentrated under reduced pressure to provide 14 g of dextranylglucuronic acid as white powder. HPLC analysis of this product (conditions: Asahi Pack GS320 (o/7.6×50 mm, Asahi Kasei), mobile phase, water 1 ml/min, detection: RI (Waters 410) and 200 nm (Tosoh UV-8020), sample, 20 μl of 0.5% aq. solution) gave a single peak at Rt=8.48 (Rt of starting dextran=10.83).

For the structural identification of this product, an enzymatic digestion experiment was carried out. Thus, 100 μl of glucoamylase (Wako Pure Chemical) solution (4 mg/ml) was added to 100 μl of a 1.5% aqueous solution of the above product and the mixture was incubated at 30° C. for 24 hours. This enzymatic digest was analyzed by HPLC. As control, dextran-4 was also subjected to glucoamylase treatment. The results indicated that the product of this example was not digested by glucoamylase. On the other hand, dextran-4 was digested by glucoamylase so that the substrate disappeared while glucose was produced. Based on the above findings, the product was identified to be dextranylglucuronic acid of formula (VIII) (wherein n=15).

EXAMPLE 19

In the same manner as Example 1, *Pseudogluconobacter saccharoketogenes* K591S was cultured in peptone yeast (PY) medium containing 1% Bactopeptone and 1% yeast extract at 30° C. on a rotary shaker at 230 rpm at pH 7.5 for 3 days. The resultant culture was transferred to a main culture peptone-yeast medium (PY) and incubated at 30° C. with addition of 0.1% calcium chloride under shaking at 230 rpm for 48 hours. The resultant culture broth was centrifuged at 10000 rpm for 10 minutes. The cell pellet was washed with 500 ml of water to recover 7.5 g of cells per liter of broth. Then, 30 g of dextran-4 (mol. wt. 4000–6000, Extra Synthese, France) was dissolved in 1 l of water and a suspension of 56 g wet cells in 1 l of water was added. The reaction was carried out at 32° C. under stirring at 800 rpm and aeration at 60 ml/min, with addition of 0.1% NaOH solution so as to control the system at pH 6.3, for 6.5 hours. The reaction mixture was centrifuged and the supernatant, 2 l, was recovered and passed through a membrane filter for removal of cellular components. The filtrate was applied to an HP-20 column (900 ml) and the column was washed with 2000 ml of water. The effluent was acidified with concentrated hydrochloric acid and filtered through a membrane filter. The filtrate was applied to an SP-205 column (100 ml) and after the column was washed with 0.05 M HCl (1000 ml) and, then, with water (2000 ml), elution was carried out with 20% MeOH (2000 ml). The eluate was concentrated and lyophilized to provide 14 g of dextranylgluconic acid as white powder. HPLC analysis of this product (conditions: Asahi Pack GS 320 (o/7.6 mm×50 mm, Asahi Kasei); mobile phase, water 1 ml/min; RI (Waters 410) and 200 nm (Tosoh UV-8020), sample 20 μl of 0.5% aq. sol.) showed a single peak at Rt=8.70. When this product was digested with glucoamylase under the conditions described above, it was readily digested, giving rise to glucose and glucosylgluconic acid. Therefore, this compound was identified to be dextranylgluconic acid.

EXAMPLE 20

As in Example 19, *Pseudogluconobacter saccharoketogenes* was cultured and 50 g of the cells (wet cells) were added to a solution of 30 g dextranylglucuronic acid (prepared by the procedure of Example 18) in 1 l of water. The reaction was conducted at 32° C. under stirring at 800 rpm and aeration at 60 ml/min. for 21 hours, with 0.1% NaOH solution being gradually added so as to control the reaction system at pH 6.3. The reaction mixture was centrifuged and the supernatant, 2 l, was filtered through a membrane filter to further remove the cells. The filtrate was applied to an HP-20 column (900 ml) and elution was carried out with 1.5 l of water. The eluate was concentrated and lyophilized to provide 12 g of sodium salt of glucuronyldextranylgluconic acid of general formula (IX) as white powder.

HPLC: Rt=9.12, one peak

HPLC parameters and settings: column GS-320, mobile phase $H_2O$, flow rate 1 ml/min, detection RI $^{13}$C-NMR ($D_2O$) δ: 179.554, 178.119, 172.434 with an intensity ratio of 1:0.5:0.5. The peak at 179.554 was assigned to the carbonyl-C of the glucuronyl moiety and the other peaks to the carbonyl-C of the gluconic acid moiety (partial lactonization was assumed).

EXAMPLE 21

A 50% aqueous solution of ferric chloride hexahydrate, 50 ml, was warmed to 30° C. and 50 ml of 24% $Ha_2CO_3$ solution was added dropwise thereto under stirring at 0.4 ml/min. Then, 50 ml of a 10% solution of the dextranylglucuronic acid of Example 18 was added dropwise at 3 ml/min, with 16% $Na_2CO_3$ solution being added portionwise at the rate of 0.4 ml/min. so as to control the reaction system at pH 4.3. Then, 200 ml of ethanol was added and the mixture was stirred well to prepare a slurry. This slurry was centrifuged (5000 rpm) and the pellet was recovered and dissolved in 40 ml of water. This solution was stirred well with 60 ml of ethanol and the mixture was centrifuged to remove the soluble fraction. The precipitate was evenly dispersed in 20 ml of water and using an evaporator, the ethanol was removed under reduced pressure. The residue was adjusted to pH 5-6 by adding 10% NaOH solution at the rate of 0.2 ml/min. under vigorous stirring, after which it was heated at 100° C. for 20 minutes. Then, phenol was added at a final concentration of 4 mg/ml to provide 22 ml of dextranylgluconic acid-iron hydroxide sol. Intramuscular administration of 1 ml of this product to young pigs produced marked improvements in anemic symptoms. A glucuronyldextranylglucuronic acid-iron hydroxide sol could also be produced in the same manner and showed a significant ameliorating effect on anemia in young pigs.

EXAMPLE 22

Production of dextranylgluconic acid-iron hydroxide sol

In 100 ml of water was dissolved 100 g of ferric chloride, ($FeCl_3.6H_2O$) and the solution was sonicated with Branson B-220 for 1 hour to obtain a homogeneous solution. This solution was made up with water to 200 ml and transferred to a 500 ml beaker. Under thorough stirring at 30° C., 200 ml of 24% sodium carbonate solution was added at the rate of 0.8 ml/min. to provide a light yellow-brown ferric hydroxide sol.

This ferric hydroxide sol, 100 ml, was taken in a 300 ml beaker and under thorough stirring at 30° C., 50 ml of 10% dextranylgluconic acid solution was gradually added. Then, 16% $NaCO_3$ solution was added very slowly at the rate of 0.1~0.2 ml/min. to adjust the mixture to pH 4.3. Then, 200 ml of ethanol was added with stirring and the resultant precipitate was recovered by centrifuging and suspended evenly in 80 ml of water. To this suspension was added 120 ml of ethanol for reprecipitation and the precipitate was collected by centrifugation. This procedure was carried out once again and the final precipitate was suspended in 20 ml of water. Under thorough stirring, 10% NaOH solution was added at the rate of 0.1-0.2 ml/min. until the pH became 6.0. This solution was autoclaved at 120° C. for 10 minutes, after which phenol (final conc. 1%) was added as the preservative. The solution was then concentrated in an evaporator to provide a dextranylgluconic acid-ion hydroxide sol. This sol was found to be very stable. Its properties were as follows.

Total iron salt: 200 mg/ml, viscosity 32 cP, electrical conductivity 47 mS/cm.

EXAMPLE 23

Dialytic conversion of dextranylglucuronic acid to iron salt

A 50% aqueous solution of ferric chloride hexahydrate, 50 ml, was warmed to 30° C. To this solution was added 50 ml of 24% $Na_2CO_3$ solution portionwise at the rate of 0.30 ml/min. with vigorous stirring to provide a blackish ocher-colored iron hydroxide sol (pH 1.54). This iron hydroxide sol was transferred to a dialysis tube and dialyzed against ultrapure water overnight. This iron hydroxide sol dialyzate, about 170 ml, was black-brown and showed a pH value of 4.47.

To this iron hydroxide sol dialyzate was added 50 ml of a 10% aqueous solution of the dextranylglucuronic acid obtained in Example 18 and the mixture was stirred thoroughly and adjusted to pH 4.3 with 16% $Na_2CO_3$ solution. The mixture was then autoclaved at 100° C. for 30 minutes, after which it was adjusted to pH 12 with 10% NaOH solution. This mixture was autoclaved again at 121° C. for 20 minutes for thorough dissolution to provide a black-brown dextranylglucuronic acid-ferric hydroxide complex solution. This complex solution was dialyzed by overnight dialysis using the same dialysis tube as above and, then, phenol was added at a final concentration of 4 mg/ml to provide 22 ml of an injectable sol of dextranylglucuronic acid-ferric hydroxide complex. This product was a stable sol having the following properties. Total iron salt concentration; 201 mg/ml, viscosity 23.9 cP, electrical conductivity 3.7 mS/cm.

Intramuscular administration of this product, 1 ml, to anemic young swine resulted in a marked improvement in anemic symptoms.

Dextranylgluconic acid-ferric hydroxide complex could also be produced in the same manner as above. This complex was also found to produce a marked improvement in anemia in young swine.

EXAMPLE 24

In the same manner as Example 11, a Viot's 5-liter jar fermenter was charged with 1 l of *Pseudogluconobacter saccharoketogenes* cell suspension and 30 g of rebaudioside-A, followed by addition of 1.5 l of sterilized water and 400 ml of IRA-68 to prepare a reaction system. While this system was stirred at 600 rpm (32° C.), air was bubbled through the mixture at 1.6 l/min. The rebaudioside-A disappeared from the supernatant fluid in one hour. The reaction was, therefore, terminated and the reaction mixture was centrifuged to separate the supernatant from the IRA -68. The IRA-68 was filled into a column (o/4×40 cm) and elution was carried out with 2N-sodium chloride solution (8.1 l). The eluate was applied to an HP-20 (1 l) column for adsorption and after the column was rinsed with water (8 l), elution was carried out with 10% ~50% ethanol to provide the objective uronic acid-form rebaudioside-A sodium salt.

The above product was concentrated and lyophilized to provide 10.6 g of colorless powder. This powder was recrystallized from MeOH-H$_2$O to give 10.6 g of colorless needles m.p. 220° C. (decomp). HPLC analysis (ODP column, acetonitrile-water=30:70) of this product showed a single peak at Rt=9.70.

$^{13}$C-NMR (D$_2$O) ppm; 18.06, 21.52, 22.91, 24.19, 30.89, 39.51, 40.15, 42.02, 43.01, 43.73, 44.58, 46.69, 46.79, 49.89, 56.17, 59.64, 63.51, 63.71, 64..37, 71.36, 72.43, 73.14, 74.40, 74.67, 76.29, 76.99, 78.12, 78.70, 78.72, 78.81, 78.93, 79.27, 79.38, 81.49, 87.99, 90.31, 96.64, 98.70, 104.87, 105.06, 107.32, 155.99, 177.79, 181.64.

Based on the above data, this product was identified as sodium salt of the compound of formula (II) wherein $$R_1 = \begin{array}{c} \text{-}\beta\text{-Glc-2-}\beta\text{-Glc} \\ \backslash \\ 3\text{-}\beta\text{-Glc} \end{array}$$

compound of the following formula (X).

From the HPLC data for each of the samples obtained above, the time course of % residue of cyclodextrin was determined up to 120 minutes.

The enzymes used and their concentrations

| Enzyme | Origin | Concentration of enzyme *(units/ml) |
|---|---|---|
| α-Amylase | *Bacillus subtilis* (Wako Pure Chemical) | 20 |
| Glucoamylase | *Rhizopus* sp. (Wako Pure Chemical) | 2 |
| Pullulanase | *Klebsiella pneumoniae* (Hayashibara) | 10 |
| β-Glucuronidase | Calf liver (Wako Pure Chemical) | 700 |

"Units" is based on the unit prescribed in the indication attached to the respective commercially available enzymes.

Results

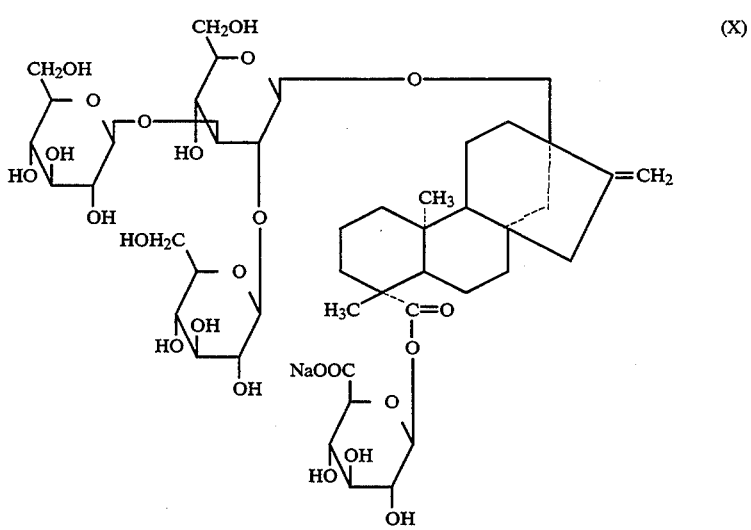

(X)

Test Example

The stability against enzymatic degradation of the 6-O-α-D-glucuronyl(1→4)-α-D-glucosyl-β-cyclodextrin Na salt (1)obtained in Example 4 was evaluated using a variety of enzymes. As a control substrate, 6-O-α-maltosyl-β-cyclodextrin was used.

Method

To aliquots of each test cyclodextrin solution (10 mM) in water were added the under-mentioned enzymes, respectively, each in a predetermined amount, and each reaction system was incubated in a water bath at 37° C. Then, 500 μl of the reaction mixture was serially sampled and heated at 100° C. for 15 minutes to inactivate the enzyme. It was then centrifuged (15,000 rpm, 5 min.) and filtered through a Millipore USY-1 filter (cutoff molecular weight 10,000). The filtrate was diluted 10-fold and analyzed by HPLC under the following conditions.

HPLC parameters and settings:
Column: NH2P-50 (Asahipak)
Mobile phase: CH$_3$CN:H$_2$O=48:52 supplemented with 0.005 M PIC reagent
Flow rate: 0.8 ml/min.
Detection: RI The time courses of % residue of 6-O-β-D-glucuronyl(14)-α-D-glucosyl-β-cyclodextrin Na (1) and 6-O-α-maltosyl-β-cyclodextrin in the treatment with respective enzymes are shown in FIG. 11 through FIG. 14.

The compound of the invention (1) was found to be more stable than the control 6-O-α-maltosyl-β-cyclodextrin against enzymatic degradation with any of α-amylase, glucoamylase and pullulanase.

Particularly in the enzymatic degradation with pullulanase, whereas the control 6-O-α-maltosyl-β-cyclodextrin was decomposed about 60%, the compound of the invention (1) remained substantially unaffected.

We claim:

1. A process for producing a saccharide carboxylic acid or a salt thereof which comprises permitting a *Pseudogluconobacter saccharoketogenes* microorganism capable of oxidizing a hydroxymethyl group and/or a hemiacetal hydroxyl-attached carbon atom to carboxyl group or a cell preparation obtained therefrom to act on a hydroxymethyl- and/or hemiacetal hydroxyl-containing monosaccharide derivative, oligosaccharide, oligosaccharide derivative, polysaccharide or polysaccharide derivative to produce and accumulate the corresponding carboxylic acid and isolating said carboxylic acid.

2. A process for producing a saccharide carboxylic acid or a salt thereof which comprises permitting a *Pseudogluconobacter saccharoketogenes* microorganism capable of oxidizing a hydroxymethyl group to carboxyl group or a cell preparation obtained therefrom to act on a hydroxymethyl-containing monosaccharide derivative, oligosaccharide, oligosaccharide derivative, polysaccharide or polysaccharide derivative to produce and accumulate the corresponding carboxylic acid and isolating said carboxylic acid.

3. The process according to claim 1 wherein the cell itself of said microorganism is employed.

4. A process for producing a saccharide carboxylic acid or a salt thereof which comprises permitting a *Pseudogluconobacter saccharoketogenes* microorganism capable of oxidizing a hemiacetal hydroxyl-attached carbon atom to carboxyl group, or a cell preparation obtained therefrom to act on a hemiacetal hydroxyl-containing monosaccharide derivative, oligosaccharide, ligosaccharide derivative, polysaccharide or polysaccharide derivative to produce and accumulate the corresponding carboxylic acid and isolating said carboxylic acid.

5. The process of claim 4 wherein the cell itself of said microorganisms is employed.

6. The process of claim 4 wherein the hemiacetal hydroxyl-containing polysaccharide is dextran.

7. The process of claim 4 wherein the hemiacetal hydroxyl-containing polysaccharide derivative is dextranylglucuronic acid.

8. The process of claim 1 wherein the hydroxylmethyl-containing oligosaccharide is sucrose.

9. The process according to claim 2 wherein the cell itself of said microorganism is employed.

* * * * *

UNITED STATES PATENT AND TRADEMARK OFFICE
CERTIFICATE OF CORRECTION

PATENT NO.  : 5,434,061
DATED       : July 18, 1997
INVENTOR(S) : TOSHIHIRO ISHIGURO, MASAHIDE OKA, TAKAMASA YAMAGUCHI and IKUO NOGAMI It is certified that error appears in the above-indentified patent and that said Letters Patent is hereby corrected as shown below:

At column 7, lines 33 to 38, correct formula (II) to read as follows:

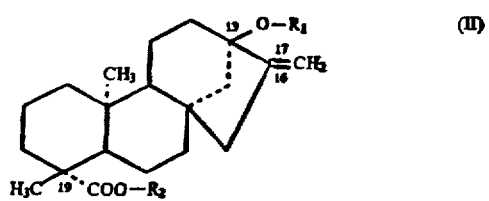

Signed and Sealed this

Nineteenth Day of May, 1998

Attest:

BRUCE LEHMAN

Attesting Officer    Commissioner of Patents and Trademarks